(12) United States Patent
Deng et al.

(10) Patent No.: US 8,217,043 B2
(45) Date of Patent: Jul. 10, 2012

(54) COMPOUNDS AND METHODS FOR THEIR USE

(75) Inventors: Shaojiang Deng, San Mateo, CA (US); Wen-Bin Ho, Los Altos, CA (US); Lee A. Flippin, Woodside, CA (US)

(73) Assignee: Fibrogen, Inc., San Francisco, CA (US)

( * ) Notice: Subject to any disclaimer, the term of this patent is extended or adjusted under 35 U.S.C. 154(b) by 237 days.

(21) Appl. No.: 12/544,861

(22) Filed: Aug. 20, 2009

(65) Prior Publication Data

US 2010/0047367 A1 Feb. 25, 2010

Related U.S. Application Data

(60) Provisional application No. 61/090,468, filed on Aug. 20, 2008.

(51) Int. Cl.
*A61K 31/50* (2006.01)
*C07D 237/00* (2006.01)

(52) U.S. Cl. ............... 514/252.06; 514/248; 514/252.01; 514/252.05; 544/238; 544/239

(58) Field of Classification Search .................. 544/238, 544/239; 514/248, 252.01, 252.05, 252.06
See application file for complete search history.

(56) References Cited

U.S. PATENT DOCUMENTS

| | | | |
|---|---|---|---|
| 7,323,475 | B2 | 1/2008 | Arend et al. |
| 7,618,940 | B2 | 11/2009 | Fourney et al. |
| 7,629,357 | B2 | 12/2009 | Arend et al. |
| 7,696,223 | B2 | 4/2010 | Deng et al. |
| 7,713,986 | B2 | 5/2010 | Seeley et al. |
| 2003/0153503 | A1 | 8/2003 | Klaus et al. |
| 2003/0176317 | A1 | 9/2003 | Guenzler-Pukall et al. |
| 2004/0204356 | A1 | 10/2004 | Guenzler-Pukall et al. |
| 2005/0020487 | A1 | 1/2005 | Klaus et al. |
| 2006/0178316 | A1 | 8/2006 | Klaus et al. |
| 2006/0183695 | A1 | 8/2006 | Klaus et al. |
| 2006/0199836 | A1 | 9/2006 | Turtle et al. |
| 2006/0258660 | A1 | 11/2006 | Guenzler-Pukall et al. |
| 2006/0258702 | A1 | 11/2006 | Guenzler-Pukall et al. |
| 2006/0270699 | A1 | 11/2006 | Guenzler-Pukall et al. |
| 2006/0276477 | A1 | 12/2006 | Klaus et al. |
| 2007/0004627 | A1 | 1/2007 | Seeley et al. |
| 2007/0155784 | A1 | 7/2007 | Arend et al. |
| 2007/0185159 | A1 | 8/2007 | Arend et al. |
| 2007/0293575 | A1 | 12/2007 | Seeley et al. |
| 2007/0298104 | A1 | 12/2007 | Arend et al. |
| 2008/0004309 | A1 | 1/2008 | Deng et al. |
| 2008/0293763 | A1 | 11/2008 | Arend et al. |

FOREIGN PATENT DOCUMENTS

| | | |
|---|---|---|
| WO | WO 02/074981 | 9/2002 |
| WO | WO 03/049686 | 6/2003 |
| WO | WO 03/053997 | 7/2003 |
| WO | WO 03/080566 | 10/2003 |
| WO | WO 2004/052284 | 6/2004 |
| WO | WO 2004/052285 | 6/2004 |
| WO | WO 2004/108121 | 12/2004 |
| WO | WO 2004/108681 | 12/2004 |
| WO | WO 2005/007192 | 1/2005 |
| WO | WO 2006/094292 | 9/2006 |
| WO | WO 2006/133391 | 12/2006 |
| WO | WO 2006/138511 | 12/2006 |
| WO | WO 2007/025169 | 3/2007 |
| WO | WO 2007/038571 | 4/2007 |
| WO | WO 2010/056767 | 5/2007 |
| WO | WO 2007/070359 | 6/2007 |
| WO | WO 2007/090068 | 8/2007 |
| WO | WO 2007/103905 | 9/2007 |
| WO | WO 2007/115315 | 10/2007 |
| WO | WO 2007/136990 | 11/2007 |
| WO | WO 2007/146425 | 12/2007 |
| WO | WO 2007/150011 | 12/2007 |
| WO | WO 2008/076425 | 6/2008 |
| WO | WO 2008/076427 | 6/2008 |
| WO | WO 2008/089051 | 7/2008 |
| WO | WO 2008/089052 | 7/2008 |
| WO | WO 2008/130508 | 10/2008 |
| WO | WO 2008/130600 | 10/2008 |
| WO | WO 2008/137060 | 11/2008 |
| WO | WO 2008/137084 | 11/2008 |
| WO | WO 2009/039321 | 3/2009 |
| WO | WO 2009/039322 | 3/2009 |
| WO | WO 2009/039323 | 3/2009 |
| WO | WO 2009/049112 | 3/2009 |
| WO | WO 2009/070644 | 6/2009 |
| WO | WO 2009/073497 | 6/2009 |
| WO | WO 2009/073669 | 6/2009 |
| WO | WO 2009/075822 | 6/2009 |
| WO | WO 2009/075826 | 6/2009 |
| WO | WO 2009/086044 | 7/2009 |
| WO | WO 2009/089547 | 7/2009 |
| WO | WO 2010/022240 | 2/2010 |

OTHER PUBLICATIONS

Vippagunta et al., "Crystalline Solids", Adv. Drug Del. Rev., 48 (2001) 3-26.*
Wolff, M.E., "Burger's Medicinal Chemistry", 5th Ed., Part 1, pp. 975-977 (1995).*
Banker et al., "Modern Pharmaceuticals", 3rd Ed., p. 596 (1996).*
U.S. Appl. No. 12/734,895, filed Aug. 16, 2010, Arend et al.
U.S. Appl. No. 12/811,821, filed Jul. 6, 2010, Zhou et al.
U.S. Appl. No. 12/866,023, filed Sep. 14, 2010, Ho et al.
Bruegge, K. et al., "Hydroxylation of Hypoxia-Inducible Transcription Factors and Chemical Compounds Targetign the HIF-alpha Hydroxylases," Current Medicinal Chemistry, vol. 14, pp. 1853-1862, XP002517838 (2007).
Wermuth, C.G., "Molecular Variants Based on Isosteric Replacements," The Practice of Medicinal Chemistry, Elsevier, pp. 189-214, XP009112544 (2003).

* cited by examiner

*Primary Examiner* — Paul V. Ward
(74) *Attorney, Agent, or Firm* — Foley & Lardner LLP

(57) ABSTRACT

The present invention relates to novel compounds capable of modulating the stability and/or activity of hypoxia inducible factor (HIF) by inhibiting the activity of at least one HIF hydroxylase enzyme.

32 Claims, No Drawings

COMPOUNDS AND METHODS FOR THEIR USE

CROSS REFERENCE TO RELATED APPLICATIONS

This application claims the benefit under 35 U.S.C. §119(e) of U.S. Provisional Application Ser. No. 61/090,468 filed on Aug. 20, 2008, which is hereby incorporated by reference in its entirety.

BACKGROUND OF THE INVENTION

1. Field of the Invention

The present invention relates to novel compounds, methods, and compositions capable of decreasing HIF hydroxylase enzyme activity, thereby increasing the stability and/or activity of hypoxia inducible factor (HIF).

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ), also known as aryl hydrocarbon receptor nuclear transporter (ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J. Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J. Biol. Chem.* 275:25733-25741; and Tanimoto et al. (2000) *EMBO J.* 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as myocardial acute ischemia, and early infarction, pulmonary hypertension, inflammation, and anemia.

HIFα levels are also increased by a number of factors that mimic hypoxia, including iron chelators such as desferrioxamine (DFO), and divalent metal salts such as $CoCl_2$. Additionally, compounds originally identified as inhibitors of procollagen prolyl hydroxylase enzymes have been found to stabilize HIFα. Examples of such compounds can be found, e.g., in Majamaa et al. (1984) *Eur. J. Biochem.* 138:239-245; Majamaa et al. (1985) *Biochem. J.* 229:127-133; Kivirikko, and Myllyharju (1998) *Matrix Biol.* 16:357-368; Bickel et al. (1998) *Hepatology* 28:404-411; Friedman et al. (2000) *Proc. Natl. Acad. Sci. USA* 97:4736-4741; Franklin (1991) *Biochem. Soc. Trans.* 19:812-815; and Franklin et al. (2001) *Biochem. J.* 353:333-338. Additionally, compounds that inhibit HIF hydroxylase enzymes have been described in, e.g., International Publication Nos. WO 03/049686, WO 02/074981, WO 03/080566, WO 2004/108681, WO 2006/094292, WO 2007/038571, WO 2007/070359, WO 2007/090068, WO 2007/103905, WO 2007/115315, WO 2007/136990, WO 2007/150011, WO 2008/076425, WO 2008/076427, WO 2008/089051, WO 2008/089052, WO 2008/130600, WO 2008/130508, WO 2008/137084, WO 2008/137060, WO 2009/039321, WO 2009/039322, WO 2009/039323, WO 2009/049112, WO 2009/070644, WO2009/073497, WO 2009/073669, WO 2009/073669, and WO 2009/086044.

There remains a need for compounds that are effective in the treatment and prevention of conditions and disorders associated with HIF, including anemia and tissue damage caused by ischemia and/or hypoxia. The compounds provided herein inhibit HIF hydroxylase activity, thereby increasing the stability and/or activity of hypoxia inducible factor (HIF), and can be used to treat and prevent HIF-associated conditions and disorders.

SUMMARY OF THE INVENTION

The present invention is directed to novel compounds, and methods of using these compounds to inhibit HIF hydroxylase activity, thereby increasing the stability and/or activity of hypoxia inducible factor (HIF).

In one aspect, there are provided compounds of Formula I:

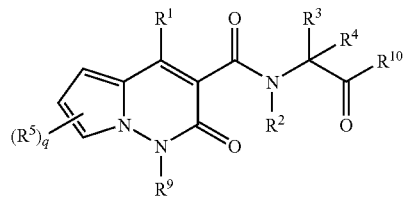

wherein:

q is 0, 1, 2 or 3;

$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino;

$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, alkyl, and substituted alkyl;

each $R^5$ independently is selected from the group consisting of hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl; or wherein any two adjacent $R^5$ groups, together with the carbon atoms attached thereto, join to form an aryl, heteroaryl or cycloalkenyl group optionally substituted with 1 to 4 substituents independently selected from halogen, alkyl, substituted alkyl, alkoxy, substituted alkoxy, aryl, and substituted aryl;

$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is —$NR^{11}R^{12}$ or —$OR^{13}$;

$R^{11}$ and $R^{12}$ independently are selected from the group consisting hydrogen, alkyl, cycloalkyl-alkyl, $C_3$-$C_8$ heterocyclic, aryl, and —$C(O)C_1$-$C_4$ alkyl;

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, tautomer or prodrug thereof.

In one embodiment, there is provided a compound of formula II:

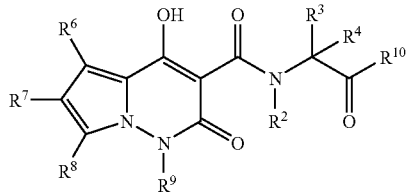

II wherein
$R^2$ is selected from the group consisting of hydrogen, alkyl and substituted alkyl $R^3$ is selected from the group consisting of hydrogen, deuterium, alkyl and substituted alkyl;

$R^4$ is selected from the group consisting of hydrogen, deuterium, alkyl, and substituted alkyl;

$R^6$, $R^7$ and $R^8$ independently are selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or wherein $R^6$ and $R^7$, or $R^7$ and $R^8$, together with the carbons to which they are attached, form a 5- or 6-membered heteroaryl group or a 6-membered aryl group, optionally substituted independently by one or two substituents selected from the group consisting of halogen, alkyl, substituted alkyl, alkoxy, substituted alkoxy, aryl, and substituted aryl;

$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is —$NR^{11}R^{12}$ or —$OR^{13}$;

$R^{11}$ and $R^{12}$ independently are selected from the group consisting hydrogen, alkyl, cycloalkyl-alkyl, $C_3$-$C_8$ heterocyclic, aryl, and —$C(O)C_1$-$C_4$ alkyl;

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, tautomer or prodrug thereof.

In one embodiment, there is provided a compound of formula III:

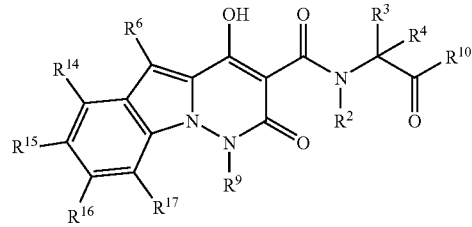

III wherein
$R^2$ is selected from the group consisting of hydrogen, alkyl and substituted alkyl $R^3$ is selected from the group consisting of hydrogen, deuterium, alkyl and substituted alkyl;

$R^4$ is selected from the group consisting of hydrogen, deuterium, alkyl, and substituted alkyl;

$R^6$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heteroocyclicthio, substituted heterocyclicthio, heteroaryl, and substituted heteroaryl;

$R^{14}$, $R^{15}$, $R^{16}$, and $R^{17}$ independently are selected from the group consisting of hydrogen, halogen, alkyl, substituted alkyl, alkoxy, substituted alkoxy, aryl, and substituted aryl;

$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is $-NR^{11}R^{12}$ or $-OR^{13}$;

$R^{11}$ and $R^{12}$ independently are selected from the group consisting hydrogen, alkyl, cycloalkyl-alkyl, $C_3$-$C_8$ heterocyclic, aryl, and $-C(O)C_1$-$C_4$ alkyl;

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, tautomer or prodrug thereof.

The invention also provides pharmaceutical compositions comprising one or more compounds of Formula I, II, or III and a pharmaceutically acceptable excipient. In some embodiments, the composition further comprises or is used in combination with at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The invention is also directed to methods of treating, pretreating, or delaying onset or progression of a condition associated with or mediated at least in part by hypoxia inducible factor (HIF), the method comprising administering to a patient a therapeutically effective amount of a compound of Formula I, II, or III or a pharmaceutical composition comprising one or more compounds of Formula I, II, or III. In one embodiment, the condition associated with or mediated by HIF is tissue damage associated with ischemia or hypoxia. In one aspect, the ischemia is associated with an event including, but not limited to, myocardial infarction, pulmonary embolism, intestinal infarction, ischemic stroke, and renal ischemic-reperfusion injury, cardiac cirrhosis, macular degeneration, chronic kidney failure, peripheral artery disease, and congestive heart failure.

The invention is also directed to methods of treating, pretreating, or delaying onset or progression of a condition associated with or mediated, at least in part, by erythropoietin (EPO), the method comprising administering to a patient a therapeutically effective amount of a compound of Formula I, II, or III or a pharmaceutical composition comprising one or more compounds of Formula I, II, or III.

The invention is also directed to methods of treating, pretreating, or delaying onset of anemia, the method comprising administering to a patient a therapeutically effective amount of a compound of Formula I, II, or III or a pharmaceutical composition comprising one or more compounds of Formula I, II, or III.

The invention is also directed to methods of inhibiting the activity of at least one HIF hydroxylase, the method comprising bringing into contact the HIF hydroxylase and a compound of the invention. In one embodiment, the HIF hydroxylase is an asparaginyl hydroxylase such as Factor Inhibiting HIF (FIH). In another embodiment, the HIF hydroxylase is a prolyl hydroxylase including, but not limited to, a HIF prolyl hydroxylase selected from the group consisting of human EGLN1, EGLN2, or EGLN3, or an orthologous enzyme from another species.

DETAILED DESCRIPTION OF THE INVENTION

Before the present compositions, and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

The invention is directed to compounds of Formula I:

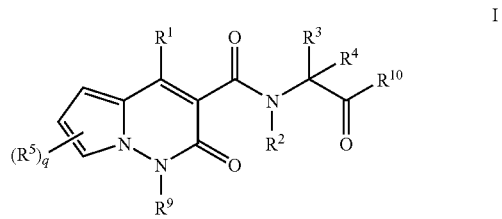

wherein:

q is 0, 1, 2 or 3;

$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino;

$R^2$ is selected from the group consisting of hydrogen, alkyl and substituted alkyl $R^3$ is selected from the group consisting of hydrogen, deuterium, alkyl and substituted alkyl;

$R^4$ is selected from the group consisting of hydrogen, deuterium, alkyl, and substituted alkyl;

each $R^5$ independently is selected from the group consisting of hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl; or wherein any two adjacent $R^5$ groups, together with the carbon atoms attached thereto, join to form an aryl, heteroaryl or cycloalkenyl group optionally substituted with 1 to 4 substituents independently selected from halogen, alkyl, substituted alkyl, alkoxy, substituted alkoxy, aryl, and substituted aryl;

$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is $-NR^{11}R^{12}$ or $-OR^{13}$;

$R^{11}$ and $R^{12}$ independently are selected from the group consisting hydrogen, alkyl, cycloalkyl-alkyl, $C_3$-$C_8$ heterocyclic, aryl, and $-C(O)C_1$-$C_4$ alkyl;

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, tautomer or prodrug thereof.

In certain embodiments, the invention is directed to compounds of Formula I wherein:

q is 0, 1, 2 or 3;

$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino;

$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, alkyl, and substituted alkyl;

each $R^5$ is independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxyl amide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;

$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is $-NR^{11}R^{12}$ or $-OR^{13}$;

$R^{11}$ and $R^{12}$ independently are selected from the group consisting hydrogen, alkyl, cycloalkyl-alkyl, $C_3$-$C_8$ heterocyclic, aryl, and $-C(O)(C_1$-$C_4$ alkyl);

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, tautomer or prodrug thereof.

In certain embodiments, q is 0. In certain embodiments, q is 1. In certain embodiments, q is 2. In certain embodiments, q is 3.

In certain embodiments, $R^1$ is hydroxy.

In some embodiments, $R^1$ is hydroxy; $R^2$ and $R^3$ are hydrogen; and each $R^5$ independently is selected from the group consisting of hydrogen, halo, alkyl, substituted alkyl, aryl, substituted aryl, alkoxy, substituted alkoxy, aryloxy, substituted aryloxy, arylthio, substituted arylthio, heteroaryl, and substituted heteroaryl.

In certain embodiments, each $R^5$ independently is selected from the group consisting of hydrogen, halo, and aryl. In some embodiments, $R^5$ is hydrogen, chloro, or phenyl.

In certain embodiments, $R^9$ is selected from the group consisting of hydrogen, alkyl, and substituted alkyl. In some embodiments, $R^9$ is selected from the group consisting of hydrogen, alkyl, $-CH_2$-aryl, $-CH_2$-substituted aryl, or $-CH_2$-heteroaryl. In certain embodiments, $R^9$ is $-CH_2$-aryl, wherein the aryl is phenyl optionally substituted with one or two halo, trifluoromethyl, alkoxy, or aryl. In certain embodiments, $R^9$ is $-CH_2$-heteroaryl, wherein the heteroaryl is pyridinyl optionally substituted with one or two halo, trifluoromethyl, alkoxy, or aryl.

In certain embodiments, the invention relates to compounds of Formula I wherein q is 1;

$R^1$ is hydroxy;

$R^2$ and $R^3$ are hydrogen;

$R^5$ is selected from the group consisting of hydrogen, halo, alkyl, substituted alkyl, aryl, substituted aryl, alkoxy, substituted alkoxy, aryloxy, substituted aryloxy, arylthio, substituted arylthio, heteroaryl, and substituted heteroaryl; and $R^{10}$ is $-OR^{13}$; wherein $R^{13}$ is hydrogen or alkyl.

In certain embodiments, the invention relates to compounds of Formula I wherein q is 1;

$R^1$ is hydroxy;

$R^2$ and $R^3$ are hydrogen;

$R^4$ is selected from the group consisting of hydrogen, methyl, and ethyl;

$R^5$ is selected from the group consisting of hydrogen, halo, and aryl;

$R^9$ is selected from the group consisting of hydrogen, alkyl, $-CH_2$-aryl, $-CH_2$-substituted aryl, or $-CH_2$-heteroaryl; and $R^{10}$ is $-OR^{13}$; wherein $R^{13}$ is hydrogen or alkyl.

In particular embodiments, the invention relates to compounds of Formula I wherein q is 0;

$R^1$ is hydroxy;

$R^2$ and $R^3$ are hydrogen;

$R^4$ is selected from the group consisting of hydrogen and methyl;

$R^9$ is $-CH_2$-aryl or $-CH_2$-substituted aryl; and $R^{10}$ is $-OR^{13}$; wherein $R^{13}$ is hydrogen or alkyl.

In particular embodiments, the invention relates to compounds of Formula I wherein
q is 0;
$R^1$ is hydroxy;
$R^2$ and $R^3$ are hydrogen;
$R^4$ is selected from the group consisting of hydrogen and methyl;
$R^9$ is hydrogen; and
$R^{10}$ is $-OR^{13}$; wherein $R^{13}$ is hydrogen or alkyl.

In certain embodiments, the invention is directed to compounds of Formula II:

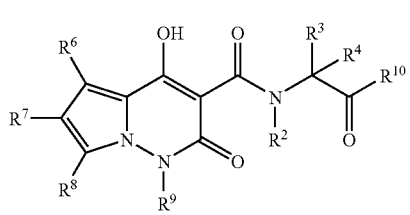

wherein
$R^2$ is selected from the group consisting of hydrogen, alkyl and substituted alkyl
$R^3$ is selected from the group consisting of hydrogen, deuterium, alkyl and substituted alkyl;
$R^4$ is selected from the group consisting of hydrogen, deuterium, alkyl, and substituted alkyl;
$R^6$, $R^7$ and $R^8$ independently are selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;
or wherein $R^6$ and $R^7$, or $R^7$ and $R^8$, together with the carbons to which they are attached, form a 5- or 6-membered heteroaryl group or a 6-membered aryl group, optionally substituted independently by one or two substituents selected from the group consisting of halogen, alkyl, substituted alkyl, alkoxy, substituted alkoxy, aryl, and substituted aryl; $R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;
$R^{10}$ is $-NR^{11}R^{12}$ or $-OR^{13}$;
$R^{11}$ and $R^{12}$ independently are selected from the group consisting hydrogen, alkyl, cycloalkyl-alkyl, $C_3$-$C_8$ heterocyclic, aryl, and $-C(O)(C_1$-$C_4$ alkyl);
or $R^{11}$ and $R^{12}$ taken together with the nitrogen to which they are attached form a 5- or 6-membered heterocyclic or substituted heterocyclic; and
$R^{13}$ is selected from the group consisting of hydrogen and alkyl which is unsubstituted or substituted with one or more substituents independently selected from the group consisting of cycloalkyl, heterocyclic, aryl, and heteroaryl;
or a pharmaceutically acceptable salt, single stereoisomer, mixture of stereoisomers, ester, tautomer or prodrug thereof.

In certain embodiments, the invention is directed to compounds of Formula II wherein:
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, alkyl, and substituted alkyl;
$R^6$, $R^7$ and $R^8$ independently are selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocycyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;
or wherein $R^6$ and $R^7$, or $R^7$ and $R^8$, together with the carbons to which they are attached, form a 5- or 6-membered heteroaryl group or a 6-membered aryl group, optionally substituted independently by one or two substituents selected from the group consisting of halogen, alkyl, substituted alkyl, alkoxy, substituted alkoxy, aryl, and substituted aryl;
$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;
$R^{10}$ is $-NR^{11}R^{12}$ or $-OR^{13}$;
$R^{11}$ and $R^{12}$ independently are selected from the group consisting hydrogen, alkyl, cycloalkyl-alkyl, $C_3$-$C_8$ heterocyclic, aryl, and $-C(O)(C_1$-$C_4$ alkyl);
or $R^{11}$ and $R^{12}$ taken together with the nitrogen to which they are attached form a 5- or 6-membered heterocyclic or substituted heterocyclic; and
$R^{13}$ is selected from the group consisting of hydrogen and alkyl which is unsubstituted or substituted with one or more substituents independently selected from the group consisting of cycloalkyl, heterocyclic, aryl, and heteroaryl;
or a pharmaceutically acceptable salt, single stereoisomer, mixture of stereoisomers, ester, tautomer or prodrug thereof.

In some embodiments, $R^6$, $R^7$ and $R^8$ independently are selected from the group consisting of hydrogen, halo, alkyl, substituted alkyl, aryl, substituted aryl, alkoxy, substituted alkoxy, aryloxy, substituted aryloxy, arylthio, substituted arylthio, heteroaryl, and substituted heteroaryl. In some embodiments, $R^6$, $R^7$ and $R^8$ independently are selected from the group consisting of hydrogen, halo, and aryl. In particular embodiments, $R^6$, $R^7$ and $R^8$ independently are selected from hydrogen, chloro, and phenyl.

In certain embodiments, the invention relates to compounds of Formula II wherein $R^2$ and $R^3$ are hydrogen;
$R^4$ is selected from the group consisting of hydrogen and methyl;
$R^6$, $R^7$, and $R^8$ independently are selected from the group consisting of hydrogen, halo, and aryl;
$R^9$ is selected from the group consisting of hydrogen, alkyl, —CH$_2$-aryl, —CH$_2$-substituted aryl, or —CH$_2$-heteroaryl; and
$R^{10}$ is —OR$^{13}$; wherein $R^{13}$ is hydrogen or alkyl.

In certain embodiments, the invention relates to compounds of Formula II wherein $R^2$, $R^3$, and $R^4$ are hydrogen;
$R^6$ and $R^8$ independently are selected from the group consisting of hydrogen and halo;
$R^7$ is selected from the group consisting of hydrogen, halo, and aryl;
$R^9$ is selected from the group consisting of hydrogen, alkyl, —CH$_2$-aryl, —CH$_2$-substituted aryl, or —CH$_2$-heteroaryl; and
$R^{10}$ is —OR$^{13}$; wherein $R^{13}$ is hydrogen or alkyl.

In certain embodiments, the invention is directed to compounds of formula III:

III wherein
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, alkyl, and substituted alkyl;
$R^6$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;
$R^{14}$, $R^{15}$, $R^{16}$, and $R^{17}$ independently are selected from the group consisting of hydrogen, halogen, alkyl, substituted alkyl, alkoxy, substituted alkoxy, aryl, and substituted aryl;
$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;
$R^{10}$ is —NR$^{11}$R$^{12}$ or —OR$^{13}$;
$R^{11}$ and $R^{12}$ independently are selected from the group consisting hydrogen, alkyl, cycloalkyl-alkyl, C$_3$-C$_8$ heterocyclic, aryl, and —C(O)(C$_1$-C$_4$ alkyl);
or $R^{11}$ and $R^{12}$ taken together with the nitrogen to which they are attached form a 5- or 6-membered heterocyclic or substituted heterocyclic; and
$R^{13}$ is selected from the group consisting of hydrogen and alkyl which is unsubstituted or substituted with one or more substituents independently selected from the group consisting of cycloalkyl, heterocyclic, aryl, and heteroaryl;
or a pharmaceutically acceptable salt, single stereoisomer, mixture of stereoisomers, ester, tautomer or prodrug thereof.

In certain embodiments of Formula I, II, and III, $R^2$ is hydrogen.

In certain embodiments of Formula I, II, and III, $R^2$ and $R^3$ are hydrogen.

In certain embodiments of Formula I, II, and III, $R^2$, $R^3$, and $R^4$ are hydrogen.

In some embodiments, $R^9$ is hydrogen.
In some embodiments, $R^9$ is alkyl.
In some embodiments, $R^9$ is a substituted alkyl selected from the group consisting of —CH$_2$-aryl, —CH$_2$-substituted aryl, —CH$_2$-cycloalkyl, —CH$_2$-substituted cycloalkyl, —CH$_2$-heterocyclic, —CH$_2$-substituted heterocyclic, —CH$_2$-heteroaryl and —CH$_2$-substituted heteroaryl. In particular embodiments, $R^9$ is —CH$_2$-aryl, —CH$_2$-substituted aryl, or —CH$_2$-heteroaryl. In some embodiments, substituted aryl is substituted with one or two fluoro, chloro, trifluoromethyl, phenyl, or methoxy.

In some embodiments, $R^{10}$ is —OR$^{13}$; and $R^{13}$ is selected from the group consisting of hydrogen and alkyl which is unsubstituted or substituted with one or more substituents independently selected from the group consisting of cycloalkyl, heterocyclic, aryl, and heteroaryl.

Compounds of the invention include, but are not limited to, [(1-Benzyl-4-hydroxy-2-oxo-1,2-dihydro-pyrrolo[1,2-b]pyridazine-3-carbonyl)-amino]-acetic acid; [(1-Benzyl-5,6,7-trichloro-4-hydroxy-2-oxo-1,2-dihydro-pyrrolo[1,2-b]pyridazine-3-carbonyl)-amino]-acetic acid; {[1-(4-Fluoro-benzyl)-4-hydroxy-2-oxo-1,2-dihydro-pyrrolo[1,2-b]pyridazine-3-carbonyl]-amino}-acetic acid; [(4-Hydroxy-2-oxo-1,2-dihydro-pyrrolo[1,2-b]pyridazine-3-carbonyl)-amino]-acetic acid; {[1-(2-Fluoro-benzyl)-4-hydroxy-2-oxo-1,2-dihydro-pyrrolo[1,2-b]pyridazine-3-carbonyl]-amino}-acetic acid; {[1-(2,4-Difluoro-benzyl)-4-hydroxy-2-oxo-1,2-dihydro-pyrrolo[1,2-b]pyridazine-3-carbonyl]-amino}-acetic acid; {[1-(2-Chloro-benzyl)-4-hydroxy-2-oxo-1,2-dihydro-pyrrolo[1,2-b]pyridazine-3-carbonyl]-amino}-acetic acid; {[1-(3-Chloro-benzyl)-4-hydroxy-2-oxo-1,2-dihydro-pyrrolo[1,2-b]pyridazine-3-carbonyl]-amino}-acetic acid; [(4-Hydroxy-1-naphthalen-2-ylmethyl-2-oxo-1,2-dihydro-pyrrolo[1,2-b]pyridazine-3-carbonyl)-amino]-acetic acid; {[4-Hydroxy-2-oxo-1-(4-trifluoromethyl-benzyl)-1,2-dihydro-pyrrolo[1,2-b]pyridazine-3-carbonyl]-amino}-acetic acid; {[1-(4-Chloro-benzyl)-4-hydroxy-2-oxo-1,2-dihydro-pyrrolo[1,2-b]pyridazine-3-carbonyl]-amino}-acetic acid; {[4-Hydroxy-1-(4-methoxy-benzyl)-2-oxo-1,2-dihydro-pyrrolo[1,2-b]pyridazine-3-carbonyl]-amino}-acetic acid; {[4-Hydroxy-2-oxo-1-(3-trifluoromethyl-benzyl)-1,2-dihydro-pyrrolo[1,2-b]pyridazine-3-carbonyl]-amino}-acetic acid; {[1-(3-Fluoro-benzyl)-4-hydroxy-2-oxo-1,2-dihydro-pyrrolo[1,2- b]pyridazine-3-carbonyl]-amino}-acetic acid; {[1-(2,6-Difluoro-benzyl)-4-hydroxy-2-oxo-1,2-dihydro-pyrrolo[1,2-b]pyridazine-3-carbonyl]-amino}-acetic acid; {[4-Hydroxy-2-oxo-1-(2-trifluoromethyl-benzyl)-1,2-dihydro-pyrrolo[1,2-b]pyridazine-3-carbonyl]-amino}-acetic acid; [(1-Butyl-4-hydroxy-2-oxo-1,2-dihydro-pyrrolo[1,2-b]pyridazine-3-carbonyl)-amino]-acetic acid; {[4-(4-Fluoro-benzyl)-1-hydroxy-3-oxo-3,4-dihydro-4,4a-diaza-fluorene-2-carbonyl]-amino}-acetic acid; 2-(S)-{[4-(4-Fluoro-benzyl)-1-hydroxy-3-oxo-3,4-dihydro-4,4a-diaza-fluorene-2-carbonyl]-amino}-propionic acid; [(1-Hexyl-4-hydroxy-2-oxo-1,2-dihydro-pyrrolo[1,2-b]pyridazine-3-carbonyl)-amino]-acetic acid; {[7-Fluoro-4-(4-fluoro-benzyl)-1-hydroxy-3-oxo-3,4-dihydro-4,4a-diaza-fluorene-2-carbonyl]-amino}-acetic acid; {[6-Chloro-4-hydroxy-2-oxo-1-(4-trifluoromethyl-benzyl)-1,2-dihydro-pyrrolo[1,2-b]pyridazine-3-carbonyl]-amino}-acetic acid; 2-(S)-{[6-Chloro-4-hydroxy-2-oxo-1-(4-trifluoromethyl-benzyl)-1,2-dihydro-pyrrolo[1,2-b]pyridazine-3-carbonyl]-amino}-propionic acid; 2-(S)-{[4-Hydroxy-2-oxo-1-(4-trifluoromethyl-benzyl)-1,2-dihydro-pyrrolo[1,2-b]pyridazine-3-carbonyl]-amino}-propionic acid; 2-(S)-{[4-Hydroxy-2-oxo-1-(4-trifluoromethyl-benzyl)-1,2-dihydro-pyrrolo[1,2-b]pyridazine-3-carbonyl]-amino}-butyric acid; {[6-Chloro-4-hydroxy-2-oxo-1-(4-fluoro-benzyl)-1,2-dihydro-pyrrolo[1,2-b]pyridazine-3-carbonyl]-amino}-acetic acid; 2-(S)-{[6-Chloro-1-(4-fluoro-benzyl)-4-hydroxy-2-oxo-1,2-dihydro-pyrrolo[1,2-b]pyridazine-3-carbonyl]-amino}-propionic acid; {[6-Chloro-1-(4-chloro-benzyl)-4-hydroxy-2-oxo-1,2-dihydro-pyrrolo[1,2-b]pyridazine-3-carbonyl]-amino}-acetic acid; 2-(S)-{[6-Chloro-1-(4-chloro-benzyl)-4-hydroxy-2-oxo-1,2-dihydro-pyrrolo[1,2-b]pyridazine-3-carbonyl]-amino}-propionic acid; 2-(S)-{[6-Chloro-1-(4-chloro-benzyl)-4-hydroxy-2-oxo-1,2-dihydro-pyrrolo[1,2-b]pyridazine-3-carbonyl]-amino}-butyric acid; {[6-Chloro-1-(4-methoxy-benzyl)-4-hydroxy-2-oxo-1,2-dihydro-pyrrolo[1,2-b]pyridazine-3-carbonyl]-amino}-acetic acid; 2-(S)-{[6-Chloro-1-(4-methoxy-benzyl)-4-hydroxy-2-oxo-1,2-dihydro-pyrrolo[1,2-b]pyridazine-3-carbonyl]-amino}-propionic acid; 2-(S)-{[6-Chloro-1-(4-methoxy-benzyl)-4-hydroxy-2-oxo-1,2-dihydro-pyrrolo[1,2-b]pyridazine-3-carbonyl]-amino}-butyric acid; 2-(S)-{[6-Chloro-1-(4-fluoro-benzyl)-4-hydroxy-2-oxo-1,2-dihydro-pyrrolo[1,2-b]pyridazine-3-carbonyl]-amino}-butyric acid; 2-(S)-[(1-Biphenyl-4-ylmethyl-6-chloro-4-hydroxy-2-oxo-1,2-dihydro-pyrrolo[1,2-b]pyridazine-3-carbonyl)-amino]-propionic acid; 2-(R)-{[6-Chloro-1-(4-phenyl-benzyl)-4-hydroxy-2-oxo-1,2-dihydro-pyrrolo[1,2-b]pyridazine-3-carbonyl]-amino}-propionic acid; {[4-Hydroxy-2-oxo-6-phenyl-1-(4-trifluoromethyl-benzyl)-1,2-dihydro-pyrrolo[1,2-b]pyridazine-3-carbonyl]-amino}-acetic acid; [(6-Chloro-4-hydroxy-2-oxo-1-pyridin-3-ylmethyl-1,2-dihydro-pyrrolo[1,2-b]pyridazine-3-carbonyl)-amino]-acetic acid; 2-(S)-[(6-Chloro-4-hydroxy-2-oxo-1-pyridin-3-ylmethyl-1,2-dihydro-pyrrolo[1,2-b]pyridazine-3-carbonyl)-amino]-propionic acid; [(6-Chloro-4-hydroxy-2-oxo-1-pyridin-2-ylmethyl-1,2-dihydro-pyrrolo[1,2-b]pyridazine-3-carbonyl)-amino]-acetic acid; 2-(S)-[(6-Chloro-4-hydroxy-2-oxo-1-pyridin-2-ylmethyl-1,2-dihydro-pyrrolo[1,2-b]pyridazine-3-carbonyl)-amino]-propionic acid; {[6,7-Dichloro-1-(4-fluoro-benzyl)-4-hydroxy-2-oxo-1,2-dihydro-pyrrolo[1,2-b]pyridazine-3-carbonyl]-amino}-acetic acid; {[4-(4-Fluoro-benzyl)-1-hydroxy-3-oxo-6-trifluoromethyl-3,4-dihydro-4,4a-diaza-fluorene-2-carbonyl]-amino}-acetic acid; and 2-(S)-{[4-(4-Fluoro-benzyl)-1-hydroxy-3-oxo-6-trifluoromethyl-3,4-dihydro-4,4a-diaza-fluorene-2-carbonyl]-amino}-propionic acid; or a pharmaceutically acceptable salt, single stereoisomer, mixture of stereoisomers, ester, tautomer or prodrug thereof.

2. Compositions and Methods of the Invention

The invention provides for use of a compound of Formula I, II, or III for the manufacture of a medicament for use in treating various conditions or disorders as described herein. In one embodiment, a pharmaceutical composition is provided comprising at least one compound of Formula I, II, or III and a pharmaceutically acceptable excipient or carrier.

In various embodiments, the medicament or pharmaceutical composition can further comprise or be used in combination with at least one additional therapeutic agent. In one embodiment, the agent is selected from the group consisting of vitamin $B_{12}$, ferrous sulfate, folic acid, and/or recombinant erythropoietin or an erythropoiesis stimulating agent (ESA).

The compounds of the present invention, or medicaments or compositions comprising the compounds, can be used to inhibit HIF hydroxylase activity, thereby modulating the stability and/or activity of HIF and activating HIF-regulated gene expression. The compound, or composition or medicament thereof, can be used in methods to treat, pretreat, or delay progression or onset of conditions mediated at least in part by HIF including, but not limited to, anemia and various aspects of ischemic and hypoxic conditions. Ischemic and hypoxic conditions may result from an event selected from, but not limited to, myocardial infarction, pulmonary embolism, intestinal infarction, ischemic stroke, acute respiratory failure, renal ischemic-reperfusion injury, cardiac cirrhosis, macular degeneration, neonatal respiratory distress syndrome, peripheral artery disease, chronic kidney failure, congestive heart failure, etc. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, transient ischemic attack, and systemic sclerosis. In still other embodiments, compounds may be administered to a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present invention, or compositions or medicaments thereof, can be used to treat, pretreat, or delay onset of anemia, such as anemia that may develop in association with various conditions or disorders. Conditions associated with anemia include, but are not limited to, acute or chronic kidney disease, diabetes, cancer, ulcers, infection with virus, e.g., HIV, bacteria, or parasites; inflammation, etc. Conditions can further include those associated with procedures or treatments including, e.g., radiation therapy, chemotherapy, dialysis, anesthesia, and surgery. Conditions associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH). The HIF hydroxylase may be a prolyl hydroxylase including, but not limited to, a prolyl hydroxylase selected from the group consisting of EGLN1, EGLN2, and EGLN3. In one embodiment, the method comprises contacting the hydroxylase with an effective amount of one or more compounds selected from the group comprising compounds of Formula I, II, or III.

3. Definitions

It must be noted that as used herein, and in the appended claims, the singular forms "a," "an," and "the" include plural references unless the context clearly dictates otherwise.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (Genbank Accession No. NP_001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) *J. Biol. Chem.* 272:19253-19260), amino acid 556 to 575 (Tanimoto et al., supra), amino acid 557 to 571 (Srinivas et al. (1999) *Biochem. Biophys. Res. Commun.* 260:557-561), and amino acid 556 to 575 (Ivan, and Kaelin (2001) *Science* 292:464-468). Further, HIFα fragments include any fragment containing at least one occurrence of the motif LXXLAP, e.g., such as occurs in the human HIF-1α native sequence from $L_{397}$ to $P_{402}$, and from $L_{559}$ to $P_{564}$.

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include anemic conditions and tissue damage or disorders associated with ischemic or hypoxic conditions.

The term "HIF hydroxylase" refers to any enzyme that modifies the alpha subunit of HIF by hydroxylation of one or more amino acid residues. HIF hydroxylases include Factor Inhibiting HIF (FIH) (GenBank Accession AAL27308; Mahon et al. (2001) *Genes Dev.* 15:2675-2686; Lando et al. (2002) *Science* 295:858-861; and Lando et al. (2002) *Genes Dev.* 16:1466-1471, which modifies at least one asparagine residue found within HIFα (Also, see, Elkins et al. (2002) *J. Biol. Chem.* C200644200.) HIF hydroxylases also include HIF prolyl hydroxylases (HIF PHs), which modify proline residues found within HIFα.

The terms "HIF prolyl hydroxylase" or "HIF PH" refer to any enzyme that modifies the alpha subunit of HIF protein by hydroxylation of one or more proline residues. Preferably, the proline residue hydroxylated by HIF PH includes the proline found within the motif LXXLAP. HIF PH includes members of the Egl-Nine (EGLN) gene family described by Taylor (2001, *Gene* 275:125-132), and characterized by Aravind, and Koonin (2001, *Genome Biol* 2: RESEARCH 0007), Epstein et al. (2001, *Cell* 107:43-54), and Bruick and McKnight (2001, *Science* 294:1337-1340). HIF PH2, as used in exemplary assays described herein (infra), may be any HIF PH2, e.g., human EGLN1 (hEGLN1, GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AAO46039); and human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retains the ability to hydroxylate at least one prolyl residue in HIFα.

The term "ischemia" refers to a deficient supply of blood to a cell, tissue, organ, etc. Ischemia is associated with a reduction in nutrients, including oxygen, delivered to tissues. Ischemia may arise due to conditions such as atherosclerosis, formation of a thrombus in an artery or vein, blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can lead to ischemia include tissue damage due to trauma or injury, such as, e.g., spinal cord injury; viral infection, which can lead to, e.g., congestive heart failure, etc. The term "ischemic condition" refer to conditions or events that are associated with or result in ischemia. Conditions associated with or resulting in ischemia include, but not limited to, an event selected from the group consisting of myocardial infarction, ischemic stroke, pulmonary embolism, perinatal hypoxia, circulatory shock including, e.g., hemorrhagic, septic, cardiogenic, etc., mountain sickness, acute respiratory failure, etc.; intestinal infarction, acute kidney failure, renal ischemia reperfusion injury, etc; atherosclerosis, chronic venous insufficiency, congestive heart failure, cardiac cirrhosis, diabetes, macular degeneration, sleep apnea, Raynaud's disease, systemic sclerosis, nonbacterial thrombotic endocarditis, occlusive artery disease, angina pectoris, transient ischemic attacks (TIAs), chronic alcoholic liver disease, chronic kidney failure, peripheral vascular disorders, ulcers, burns, chronic wounds, etc. Ischemia can also result when individuals are placed under general anesthesia, and can cause tissue damage in organs prepared for transplant.

The terms "hypoxia" and "hypoxic" refer to an environment with levels of oxygen below normal. The term "hypoxic condition" includes, but is not limited to, ischemic conditions (ischemic hypoxia) such as those listed above, wherein hypoxia results from reduced circulation; pulmonary disorders (hypoxic hypoxia) such as COPD, severe pneumonia, pulmonary edema, pulmonary hypertension, hyaline membrane disease, and the like, wherein hypoxia results from reduced oxygenation of the blood in the lungs; anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The term "anemia" as used herein refers to any abnormality or deficiency in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

The term "anemic condition" refers to any condition, disease, or disorder associated with anemia. Anemia can arise due to various conditions, for example, acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia can develop in association with radiation therapy, chemotherapy, and kidney dialysis. Anemia can also develop in HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure which result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively and refer to any condition deviating from normal.

The terms "erythropoietin" and "EPO" refer to any naturally occurring, recombinant, or synthetic erythropoietin, erythropoiesis stimulating protein (ESP), or erythropoiesis stimulating agent (ESA) including, e.g., human erythropoietin (GenBank Accession No. AAA52400; Lin et al. (1985) *Proc. Nat'l. Acad. Sci. USA* 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan NJ), Continuous erythropoiesis receptor activator (CERA; F. Hoffmann-La Roche Ltd., Basel, Switzerland), etc.

The terms "erythropoietin-associated conditions" and "conditions mediated at least in part by erythropoietin" are used inclusively and refer to any condition that can be associated with below normal, abnormal, or inappropriate modulation of erythropoietin. EPO-associated conditions include any condition wherein an increase in EPO level would provide therapeutic benefit. Erythropoietin-associated conditions include anemic conditions such as those described above.

EPO-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The terms "treating," "treatment" and the like, are used herein to mean administering a therapy to a patient in need thereof. The therapy may be administered thereby providing a prophylactic effect in terms of completely or partially preventing a disorder or sign or symptom thereof; and/or the therapy may be administered thereby providing a partial or complete cure for a disorder and/or adverse effect attributable to the disorder.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$R$^{40}$, —NR$^{40}$S(O)$_2$—NR$^{40}$-alkyl, —NR$^{40}$S(O)$_2$—NR$^4$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as, by way of example only, —CH$_2$-aryl, e.g., benzyl; —CH$_2$-substituted aryl, —CH$_2$-cycloalkyl, —CH$_2$-substituted cycloalkyl, —CH$_2$-heterocyclic, —CH$_2$-substituted heterocyclic, —CH$_2$-heteroaryl, —CH$_2$-substituted heteroaryl, benzo[1,3]-dioxol-5-ylmethyl, etc.

The term "alkylidene" or "alkylene" refers to divalent saturated aliphatic hydrocarbyl groups having from 1 to 5 carbon atoms, more preferably 1 to 3 carbon atoms, which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like. "(C$_{u-v}$)alkylene" refers to alkylene groups having from u to v carbon atoms. The alkylidene or alkylene groups include branched and straight chain hydrocarbyl groups. For example "(C$_{1-5}$)alkylene" is meant to include methylene, ethylene, propylene, 2-methylpropylene, pentylene, and the like.

The term "alkyl alcohol" refers to the group "alkyl-OH".

The term "substituted alkyl alcohol" refers to the group "substituted alkyl-OH".

The term "alkoxy" refers to the group "alkyl-O—" which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl," "amide," "carboxylamide," and the prefix "carbamoyl," "carboxamide," "substituted carbamoyl," or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components.

The term "alkynyl" refers to an acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like.

The term "acylamino" refers to the groups —NR$^{45}$C(O) alkyl, —NR$^{45}$C(O)substituted alkyl, —NR$^{45}$C(O)cycloalkyl, —NR$^{45}$C(O)substituted cycloalkyl, —NR$^{45}$C(O) alkenyl, —NR$^{45}$C(O)substituted alkenyl, —NR$^{45}$C(O) alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O-substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy" or the prefix "carbamoyloxy" or "substituted carbamoyloxy" refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)N(R$^{49}$)$_2$ where each R$^{49}$ is independently selected from the group consisting of hydrogen and alkyl.

The term "aminothiocarbonylamino" refers to the group —NR$^{49}$C(S)N(R$^{49}$)$_2$ where each R$^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic, where each R$^{51}$ is independently selected from hydrogen or alkyl, wherein each of the terms is as defined herein. In some embodiments, substituted aryl is substituted with 2-fluoro, 3-fluoro, 4-fluoro, 2,4-difluoro, 2,6-difluoro, 2-chloro, 3-chloro, 4-chloro, 2-trifluoromethyl, 3-trifluoromethyl, 4-trifluoromethyl, 2-methoxy, 3-methoxy, 4-methoxy, 3-phenyl, or 4-phenyl.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl esters" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cation" refers to the groups, including but not limited to, Na$^+$, K$^+$, Ca$^{2+}$, Mg$^{2+}$, NH$_4^+$, N(alkyl)$_4^+$, other positively charged ions, and the like.

The term "cyano" refers to the group —CN.

The term "cycloalkyl" refers to a saturated or an unsaturated but nonaromatic cyclic alkyl groups of from 3 to 10, 3 to 8, or 3 to 6 carbon atoms having single or multiple cyclic rings including, by way of example, adamantyl, cyclopropyl, cyclobutyl, cyclopentyl, cyclooctyl, cyclohexenyl and the like.

The term "substituted cycloalkyl" refers to a cycloalkyl group having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo, and preferably is fluoro or chloro.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a heteroaromatic ring. The nitrogen and/or sulfur ring atoms can optionally be oxidized to provide for the N-oxide or the sulfoxide, and sulfone derivatives. Examples of heteroaryls include but are not limited to, pyridinyl, pyrrolyl, indolyl, thiophenyl, thienyl, and furyl.

The term "substituted heteroaryl" refers to heteroaryl groups that are substituted with from 1 to 3 substituents selected from the same group of substituents defined for substituted aryl.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO$_2$.

The term "oxo" refers to the atom (=O) or (—O$^-$).

The term "sulfonyl" refers to the group —S(O)$_2$H. The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$.

The term "heterocyclyloxy" refers to the group —O-heterocyclic, and "substituted heterocyclyloxy" refers to the group —O-substituted heterocyclic.

The term "thiol" or "mercapto" refers to the group —SH.

The term "alkylsulfanyl," "alkylthio," and "thioether" refer to the groups —S-alkyl where alkyl is as defined above.

The term "substituted alkylthio," "substituted alkylsulfanyl," and "substituted alkylthio" refer to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "pharmaceutically acceptable salt" refers to pharmaceutically acceptable salts of a compound, which salts are derived from a variety of organic, and inorganic counter ions well known in the art, and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

The term "ester" refers to compounds of Formula I, II, or III that include the group —COOR$^{54}$ where R$^{54}$ is alkyl, substituted alkyl, alkoxy, or substituted alkoxy.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the invention can be present as a mixture of stereoisomers or as a single stereoisomer.

The term "tautomer" refers to alternate forms of a compound that differ in the position of a proton, such as enol keto and imine enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

The term "prodrug", as used herein, refers to compounds of Formula I, II, or III that include chemical groups which, in vivo, can be converted into the carboxylate group adjacent to the —C(R$^3$)(R$^4$) substituent and/or can be split off from the amide N-atom and/or can be split off from the R$^1$ atom to provide for the active drug; a pharmaceutically acceptable salt thereof, or a biologically active metabolite thereof. Suitable groups are well known in the art and particularly include: for the carboxylic acid moiety, a prodrug selected from, e.g., esters including, but not limited to, those derived from alkyl alcohols, substituted alkyl alcohols, hydroxy substituted aryls and heteroaryls and the like; amides, particularly amides derived from amines of the formula HNR$^{200}$R$^{210}$ where R$^{200}$ and R$^{210}$ are independently hydrogen, alkyl, substituted alkyl, aryl, substituted aryl, and the like; hydroxymethyl, aldehyde and derivatives thereof.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this invention can be prepared from readily available starting materials using, for example, the following general methods, and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Synthesis of Compounds of the Invention

The pyridazinones of this invention are prepared by, for example, the synthetic protocols illustrated in Schemes A-D.

Scheme A
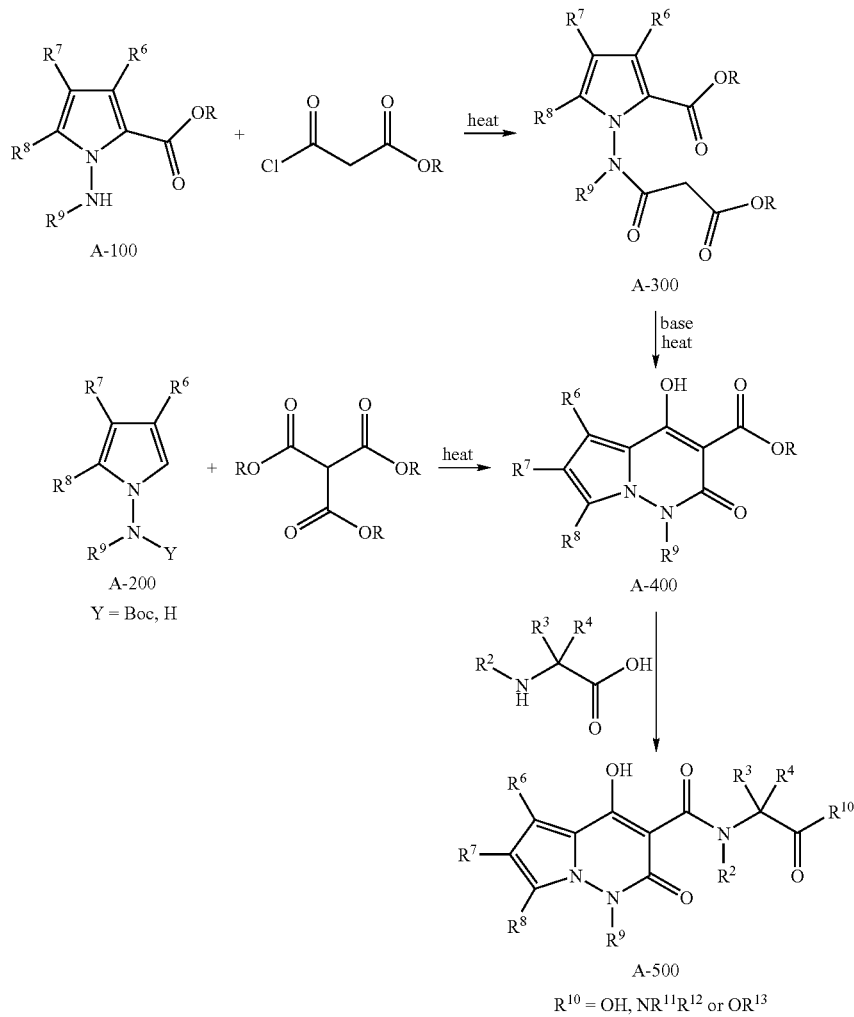
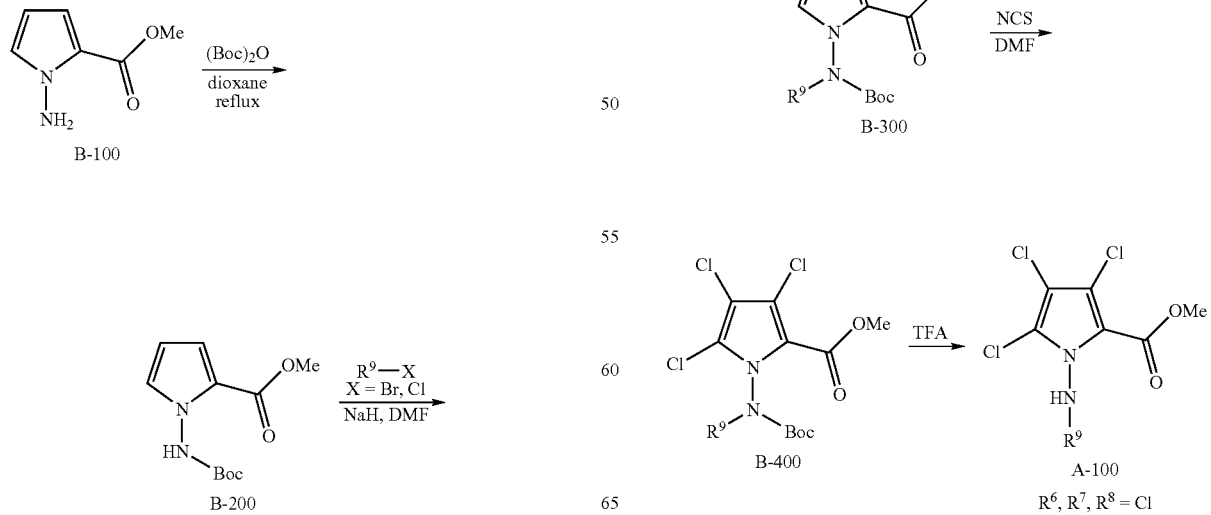

29

Scheme C

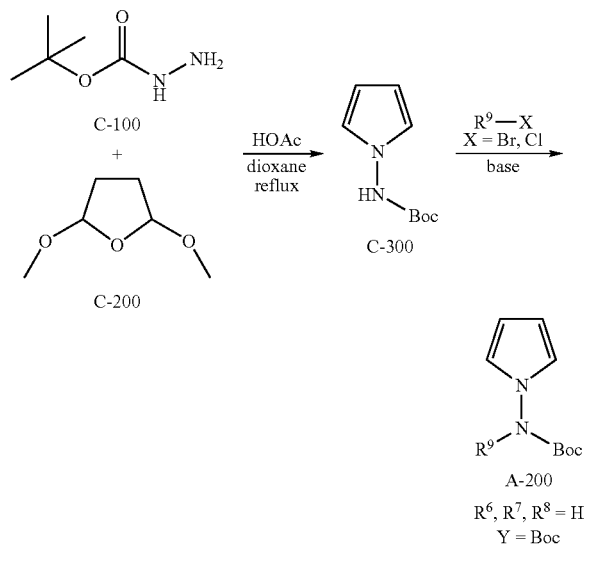

Scheme D

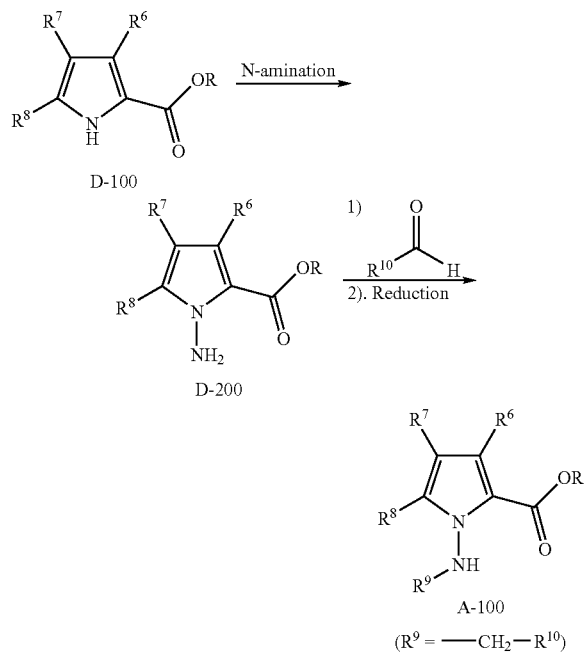

The compounds of this invention, A-500, are preferably prepared by, but are not limited to, the synthetic protocols illustrated in Scheme A. In Scheme A, the substituents $R^2$, $R^3$, $R^4$, $R^6$, $R^7$, $R^8$, $R^9$, $R^{10}$, $R^{11}$, $R^{12}$, and $R^{13}$, are as defined herein. R refers to a suitable protecting group such as methyl, ethyl, etc.

Compounds A-500 (when $R^{10}$=—OH) can be modified to A-500 (when $R^{10}$=—$NR^{11}R^{12}$) or A-500 (when $R^{10}$=—$OR^{13}$) under conventional amidation or esterification, respectively, conditions well known in the art.

Compound A-400 (wherein R refers to a suitable protecting group such as methyl, ethyl, etc.) are reacted with at least a stoichiometric amount and preferably an excess of a suitable

30 amino acid, $NHR^2$—$C(R^3)(R^4)$—$COOH(R^2, R^3,$ and $R^4$ are as defined herein, particularly, but not limited to, glycine or alanine or their corresponding salts such as sodium glycinate). The reaction is conducted under conventional coupling conditions well known in the art. In one embodiment, the reaction is conducted with or without the presence of sodium methoxide, sodium ethoxide or another suitable base in methanol, DMF, 2-methoxyethanol or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds A-500 can be recovered by conventional techniques such as neutralization, extraction, precipitation, chromatography, filtration and the like.

Compounds A-400 for use in the reactions depicted in Scheme A can be prepared either by treating compounds A-300 with a base (particularly, but not limited to, sodium methoxide or sodium ethoxide, etc.) in a suitable solvent under elevated reaction temperatures or by coupling compounds A-200 with alkoxycarbonyl-malonic acid dialkyl ester under elevated temperature.

Compounds A-300 for use in the reactions depicted in Scheme A can be prepared by coupling of compounds A-100 with chlorocarbonyl acetic acid alkyl ester in a suitable solvent (particularly, but not limited to, dioxane) under elevated temperature or in the presence of a suitable base (particularly, but not limited to, triethylamine) in a suitable solvent (particularly, but not limited to, dichloromethane) under ambient temperature.

Both compounds A-100 and A-200 are either commercially available or can be prepared according to the literature reference. In one embodiment, compounds A-100 (when $R^6$, $R^7$, $R^8$=Cl) were prepared from literature known compound B-100 (Jacobi, P. et al *Tetrahedron Lett.* 1988, 29(38), 4823-4826) by the following reaction sequence depicted in Scheme B. The Boc-protected compound B-200, obtained by reacting B-100 with $(Boc)_2O$ under elevated temperature, was alkylated with alkyl bromide or alkyl chloride to provide compounds B-300. Compounds B-300 were chlorinated by reacting with NCS to provide compounds B-400 which were then treated with TFA under ambient temperature to provide compounds A-100 (when $R^6$, $R^7$, $R^8$=Cl). In another embodiment, compounds A-200 (when $R^6$, $R^7$, $R^8$=H) were prepared from commercially available compounds C-100 and C-200 by the reaction sequence depicted in Scheme C. Compound C-100 was coupled with compound C-200 in the presence of acetic acid to provide C-300 which was then alkylated with alkyl bromide or alkyl chloride to provide compounds A-200 (when $R^6$, $R^7$, $R^8$=H).

In another embodiment, compounds A-100 ($R^9$=$CH_2$—$R^{10}$) were prepared from either commercial available or literature known compounds D-100 by the following reaction sequence depicted in Scheme D. D-100 was N-aminated following the known protocol (Bhattacharya, A. et al, *Tetrahedron Letter* 2000, 47, 5241-5343) to provide compounds D-200 which was then alkylated via reductive N-alkylation with aldehydes ($R^{10}$—CHO) to provide compounds A-100 ($R^9$=$CH_2$—$R^{10}$).

Other modifications to arrive at compounds of this invention are well within the skill of the art. For example, modification of the hydroxy group that is gamma to the nitrogen of the 5,6-membered bicyclic ring may be done by conventional means to corresponding ethers, etc.

5. Use of Compounds of the Invention

The compounds of the present invention can be used to inhibit HIF hydroxylase activity, thereby modulating the stability and/or activity of HIF and activating HIF-regulated gene expression. The compounds can be used in methods to treat, pretreat, or delay progression or onset of conditions associated with HIF including, but not limited to, anemia and various aspects of ischemic and hypoxic conditions. In various embodiments, the compound is administered immediately following a condition associated with ischemia, e.g., myocardial infarction, pulmonary embolism, intestinal infarction, ischemic stroke, renal ischemic-reperfusion injury, cardiac cirrhosis, macular degeneration, pulmonary embolism, acute respiratory failure, neonatal respiratory distress syndrome, and congestive heart failure. In another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present invention can be used to increase endogenous erythropoietin (EPO). The compounds can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

6. Testing and Administration

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-Based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 µL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, Methods Enzymol. 82:245-304). Assay reactions contain 50 mM HEPES (pH 7.4), 100 µM α-ketoglutaric acid sodium salt, 0.30 µCi/mL ketoglutaric acid α-[1-$^{14}$C]-sodium salt, 40 µM $FeSO_4$, 1 mM ascorbate, 1541.8 units/mL Catalase, with or without 50 µM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

Representative compounds of the invention were analyzed using the HIF-PH assay described above. Table 1 presents enzyme inhibition data for exemplary compounds against HIF-PH2, a representative HIF prolyl hydroxylase. By inhibiting HIF prolyl hydroxylase, compounds of the invention stabilize HIFα, which then combines with HIFβ to form an active transcription factor that increases expression of various genes involved in numerous beneficial cellular processes.

TABLE 1

| No. | Name | Concentration (μM) | % Inhibition HIF PH2 |
|---|---|---|---|
| 1 | [(1-Benzyl-4-hydroxy-2-oxo-1,2-dihydro-pyrrolo[1,2-b]pyridazine-3-carbonyl)-amino]-acetic acid | 200 | 100 |
| 2 | [(1-Benzyl-5,6,7-trichloro-4-hydroxy-2-oxo-1,2-dihydro-pyrrolo[1,2-b]pyridazine-3-carbonyl)-amino]-acetic acid | 22 | 99 |
| 3 | {[1-(4-Fluoro-benzyl)-4-hydroxy-2-oxo-1,2-dihydro-pyrrolo[1,2-b]pyridazine-3-carbonyl]-amino}-acetic acid | 200 | 100 |
| 4 | [(4-Hydroxy-2-oxo-1,2-dihydro-pyrrolo[1,2-b]pyridazine-3-carbonyl)-amino]-acetic acid | 125 | 84 |
| 5 | {[1-(2-Fluoro-benzyl)-4-hydroxy-2-oxo-1,2-dihydro-pyrrolo[1,2-b]pyridazine-3-carbonyl]-amino}-acetic acid | 125 | 96 |
| 6 | {[1-(2,4-Difluoro-benzyl)-4-hydroxy-2-oxo-1,2-dihydro-pyrrolo[1,2-b]pyridazine-3-carbonyl]-amino}-acetic acid | 200 | 100 |
| 7 | {[1-(2-Chloro-benzyl)-4-hydroxy-2-oxo-1,2-dihydro-pyrrolo[1,2-b]pyridazine-3-carbonyl]-amino}-acetic acid | 200 | 100 |
| 8 | {[1-(3-Chloro-benzyl)-4-hydroxy-2-oxo-1,2-dihydro-pyrrolo[1,2-b]pyridazine-3-carbonyl]-amino}-acetic acid | 200 | 100 |
| 9 | [(4-Hydroxy-1-naphthalen-2-ylmethyl-2-oxo-1,2-dihydro-pyrrolo[1,2-b]pyridazine-3-carbonyl)-amino]-acetic acid | 200 | 100 |
| 10 | {[1-(4-Trifluoromethyl-benzyl)-4-hydroxy-2-oxo-1,2-dihydro-pyrrolo[1,2-b]pyridazine-3-carbonyl]-amino}-acetic acid | 200 | 100 |
| 11 | {[1-(4-Chloro-benzyl)-4-hydroxy-2-oxo-1,2-dihydro-pyrrolo[1,2-b]pyridazine-3-carbonyl]-amino}-acetic acid | 200 | 100 |
| 12 | {[1-(4-Methoxy-benzyl)-4-hydroxy-2-oxo-1,2-dihydro-pyrrolo[1,2-b]pyridazine-3-carbonyl]-amino}-acetic acid | 200 | 100 |
| 13 | {[1-(3-Trifluoromethyl-benzyl)-4-hydroxy-2-oxo-1,2-dihydro-pyrrolo[1,2-b]pyridazine-3-carbonyl]-amino}-acetic acid | 125 | 97 |
| 14 | {[1-(3-Fluoro-benzyl)-4-hydroxy-2-oxo-1,2-dihydro-pyrrolo[1,2-b]pyridazine-3-carbonyl]-amino}-acetic acid | 125 | 98 |
| 15 | {[1-(2,6-Difluoro-benzyl)-4-hydroxy-2-oxo-1,2-dihydro-pyrrolo[1,2-b]pyridazine-3-carbonyl]-amino}-acetic acid | 125 | 94 |
| 16 | {[1-(2-Trifluoromethyl-benzyl)-4-hydroxy-2-oxo-1,2-dihydro-pyrrolo[1,2-b]pyridazine-3-carbonyl]-amino}-acetic acid | 125 | 98 |
| 17 | [(1-Butyl-4-hydroxy-2-oxo-1,2-dihydro-pyrrolo[1,2-b]pyridazine-3-carbonyl)-amino]-acetic acid | 50 | 97 |
| 18 | {[4-(4-Fluoro-benzyl)-1-hydroxy-3-oxo-3,4-dihydro-4a-diaza-fluorene-2-carbonyl]-amino}-acetic acid | 50 | 96 |
| 19 | 2-(S)-{4-(4-Fluoro-benzyl)-1-hydroxy-3-oxo-3,4-dihydro-4,4a-diaza-fluorene-2-carbonyl]-amino}-propionic acid | 50 | 99 |
| 20 | [(1-Hexyl-4-hydroxy-2-oxo-1,2-dihydro-pyrrolo[1,2-b]pyridazine-3-carbonyl)-amino]-acetic acid | 50 | 97 |
| 21 | {[7-Fluoro-4-(4-fluoro-benzyl)-1-hydroxy-3-oxo-3,4-dihydro-4,4a-diaza-fluorene-2-carbonyl]-amino}-acetic acid | 50 | 99 |
| 22 | {[6-Chloro-4-hydroxy-2-oxo-1-(4-trifluoromethyl-benzyl)-1,2-dihydro-pyrrolo[1,2-b]pyridazine-3-carbonyl]-amino}-acetic acid | 50 | 98 |
| 23 | 2-(S)-{[6-Chloro-4-hydroxy-2-oxo-1-(4-trifluoromethyl-benzyl)-1,2-dihydro-pyrrolo[1,2-b]pyridazine-3-carbonyl]-amino}-propionic acid | 50 | 98 |
| 24 | 2-(S)-{[4-Hydroxy-2-oxo-1-(4-trifluoromethyl-benzyl)-1,2-dihydro-pyrrolo[1,2-b]pyridazine-3-carbonyl]-amino}-propionic acid | 50 | 98 |
| 25 | 2-(S)-{[4-Hydroxy-2-oxo-1-(4-trifluoromethyl-benzyl)-1,2-dihydro-pyrrolo[1,2-b]pyridazine-3-carbonyl]-amino}-butyric acid | 200 | 98 |
| 26 | {[6-Chloro-4-hydroxy-2-oxo-1-(4-fluoro-benzyl)-1,2-dihydro-pyrrolo[1,2-b]pyridazine-3-carbonyl]-amino}-acetic acid | 67 | 98 |
| 27 | 2-(S)-{[6-Chloro-1-(4-fluoro-benzyl)-4-hydroxy-2-oxo-1,2-dihydro-pyrrolo[1,2-b]pyridazine-3-carbonyl]-amino}-propionic acid | 67 | 95 |
| 28 | {[6-Chloro-1-(4-chloro-benzyl)-4-hydroxy-2-oxo-1,2-dihydro-pyrrolo[1,2-b]pyridazine-3-carbonyl]-amino}-acetic acid | 67 | 100 |
| 29 | 2-(S)-{[6-Chloro-1-(4-chloro-benzyl)-4-hydroxy-2-oxo-1,2-dihydro-pyrrolo[1,2-b]pyridazine-3-carbonyl]-amino}-propionic acid | 67 | 100 |
| 30 | 2-(S)-{[6-Chloro-1-(4-chloro-benzyl)-4-hydroxy-2-oxo-1,2-dihydro-pyrrolo[1,2-b]pyridazine-3-carbonyl]-amino}-butyric acid | 67 | 94 |
| 31 | {[6-Chloro-1-(4-methoxy-benzyl)-4-hydroxy-2-oxo-1,2-dihydro-pyrrolo[1,2-b]pyridazine-3-carbonyl]-amino}-acetic acid | 67 | 100 |

TABLE 1-continued

| No. | Name | Concentration (μM) | % Inhibition HIF PH2 |
|---|---|---|---|
| 32 | 2-(S)-{[6-Chloro-1-(4-methoxy-benzyl)-4-hydroxy-2-oxo-1,2-dihydro-pyrrolo[1,2-b]pyridazine-3-carbonyl]-amino}-propionic acid | 67 | 97 |
| 33 | 2-(S)-{[6-Chloro-1-(4-methoxy-benzyl)-4-hydroxy-2-oxo-1,2-dihydro-pyrrolo[1,2-b]pyridazine-3-carbonyl]-amino}-butyric acid | 67 | 88 |
| 34 | 2-(S)-{[6-Chloro-1-(4-fluoro-benzyl)-4-hydroxy-2-oxo-1,2-dihydro-pyrrolo[1,2-b]pyridazine-3-carbonyl]-amino}-butyric acid | 67 | 86 |
| 35 | 2-(S)-[(1-Biphenyl-4-ylmethyl-6-chloro-4-hydroxy-2-oxo-1,2-dihydro-pyrrolo[1,2-b]pyridazine-3-carbonyl)-amino]-propionic acid | 67 | 100 |
| 36 | 2-(R)-{[6-Chloro-1-(4-phenyl-benzyl)-4-hydroxy-2-oxo-1,2-dihydro-pyrrolo[1,2-b]pyridazine-3-carbonyl]-amino}-propionic acid | 67 | 98 |
| 37 | {[4-Hydroxy-2-oxo-6-phenyl-1-(4-trifluoromethyl-benzyl)-1,2-dihydro-pyrrolo[1,2-b]pyridazine-3-carbonyl]-amino}-acetic acid | 67 | 99 |
| 38 | [(6-Chloro-4-hydroxy-2-oxo-1-pyridin-3-ylmethyl-1,2-dihydro-pyrrolo[1,2-b]pyridazine-3-carbonyl)-amino]-acetic acid | 67 | 99 |
| 39 | 2-(S)-[(6-Chloro-4-hydroxy-2-oxo-1-pyridin-3-ylmethyl-1,2-dihydro-pyrrolo[1,2-b]pyridazine-3-carbonyl)-amino]-propionic acid | 67 | 97 |
| 40 | [(6-Chloro-4-hydroxy-2-oxo-1-pyridin-2-ylmethyl-1,2-dihydro-pyrrolo[1,2-b]pyridazine-3-carbonyl)-amino]-acetic acid | 50 | 95 |
| 41 | 2-(S)-[(6-Chloro-4-hydroxy-2-oxo-1-pyridin-2-ylmethyl-1,2-dihydro-pyrrolo[1,2-b]pyridazine-3-carbonyl)-amino]-propionic acid | 50 | 91 |
| 42 | {[6,7-Dichloro-1-(4-fluoro-benzyl)-4-hydroxy-2-oxo-1,2-dihydro-pyrrolo[1,2-b]pyridazine-3-carbonyl]-amino}-acetic acid | 50 | 95 |
| 43 | {[4-(4-Fluoro-benzyl)-1-hydroxy-3-oxo-6-trifluoromethyl-3,4-dihydro-4,4a-diaza-fluorene-2-carbonyl]-amino}-acetic acid | 50 | 99 |
| 44 | 2-(S)-{[4-(4-Fluoro-benzyl)-1-hydroxy-3-oxo-6-trifluoromethyl-3,4-dihydro-4,4a-diaza-fluorene-2-carbonyl]-amino}-propionic acid | 67 | 89 |

7. Pharmaceutical Formulations and Routes of Administration

The compositions of the present invention can be delivered directly or in pharmaceutical compositions or medicaments along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro-) suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

μL=Microliter
μM=micromolar
$Boc_2O$=tert-butoxycarbonyl anhydride
br=broad
$CDCl_3$=Deuterated chloroform
d=Doublet
dd=Double doublet
dt=doublet of triplets
DCM=Dichloromethane
DMA=N,N-dimethyl acetamide
DMF=Dimethyl formamide
DMSO=Dimethyl sulfoxide
EDTA=Ethylenediamine tetraacetic acid
eq=equivalent
ESI MS=Electrospray Ionization Mass Spectrometry
EtOAc=Ethyl acetate
g=Gram
h=Hour
HCl=Hydrochloric acid
HOAc=Acetic acid
Hz=Hertz
m=Multiplet
m/z=mass to charge ratio
MeOH=Methanol
mg=Milligram
$MgSO_4$=Magnesium sulfate
MHz=Mega Hertz
min=Minute
mL=Milliliter
mM=Millimolar
mmol=Millimole
mol=Mole
MTBE=Methyl tert-butyl ether
NaCl=Sodium chloride
$NaHCO_3$=Sodium bicarbonate
NaOCl=Sodium hypochlorite
NaOMe=Sodium methoxide
NCS=N-chlorosuccinamide
NMP=N-Methyl-2-pyrrolidone
NMR=Nuclear magnetic resonance
q=quartet
rt=Room temperature
s=singlet
sat=saturated
t=triplet
TFA=Trifluoroacetic acid
THF=Tetrahydrofuran
TMSOTf=Trimethylsilyl trifluoromethanesulfonate
TLC=Thin layer chromatography
v=volume Example 1

[(1-Benzyl-4-hydroxy-2-oxo-1,2-dihydro-pyrrolo[1,2-b]pyridazine-3-carbonyl)-amino]-acetic acid a) Pyrrol-1-yl-carbamic acid tert-butyl ester A mixture of tert-butyl carbazate (5.51 g, 41.7 mmol), 2,5-dimethoxytetrahydrofuran (6.5 mL, 50.0 mmol) and acetic acid (33.6 mL) in dioxane (80 mL) was refluxed for 3 h; then cooled, the dark brown reaction mixture was concentrated, the resulting residue was directly silica gel column purified (eluents: 10% EtOAc in hexanes to 50% EtOAc in hexanes) to give the desired product (951 mg) as white solid. $^1$H NMR (CDCl$_3$, δ in ppm): 7.17 (s, br, 1H), 6.66 (m, 2H), 6.11 (m, 2H), 1.49 (s, 9H).

b) Benzyl-pyrrol-1-yl-carbamic acid tert-butyl ester

Sodium hydride (313 mg, 7.83 mmol, 60% purity in mineral oil) was added in one portion to a stirred, ice/water-cooled solution of pyrrol-1-yl-carbamic acid tert-butyl ester (951 mg, 5.22 mmol) and benzyl bromide (745 µL, 6.26 mmol) in DMF (20 mL); the mixture was stirred in the cold bath for 30 min, at which time TLC showed complete disappearance of starting material; then poured into diluted, cold ammonium chloride solution to quench the reaction, followed by extraction with EtOAc, then washed with water, and brine; then the organic phase was dried over anhydrous sodium sulfate, filtered, concentrated, and the residue was silica gel column purified to give desired product (1.376 g) as a clear oil. ESI (m/z): 273 (M+H)$^+$.

c) 1-Benzyl-4-hydroxy-2-oxo-1,2-dihydro-pyrrolo[1,2-b]pyridazine-3-carboxylic acid ethyl ester A mixture of benzyl-pyrrol-1-yl-carbamic acid tert-butyl ester (1.28 g, 4.70 mmol) and 2-ethoxycarbonyl-malonic acid diethyl ester (3.0 mL) in a test tube was heated in an oil bath (bath temperature: 220° C. to 230° C.) for 10 min; TLC (EtOAc/hexanes:1/1 by volume) showed good conversion; then cooled, the reaction mixture was directly purified with silica gel column to give the desired product as brown solid (1.00 g). ESI (m/z): 313 (M+H)$^+$.

d) [(1-Benzyl-4-hydroxy-2-oxo-1,2-dihydro-pyrrolo[1,2-b]pyridazine-3-carbonyl)-amino]-acetic acid A mixture of 1-benzyl-4-hydroxy-2-oxo-1,2-dihydro-pyrrolo[1,2-b]pyridazine-3-carboxylic acid ethyl ester (78 mg, 0.249 mmol) and sodium glycinate (122 mg, 1.25 mmol) in 2-methoxyethanol (5 mL) was refluxed for 20 h; subsequently, the reaction was cooled and solvent was removed by rotovaping; the residue was dissolved in water and then acidified with 2 M HCl solution; the precipitates were collected via filtration, washed with water and vacuum dried at 50° C. to give the desired product (64 mg) as yellow solid. ESI (m/z): 342 (M+H)$^+$.

Example 2

[(1-Benzyl-5,6,7-trichloro-4-hydroxy-2-oxo-1,2-dihydro-pyrrolo[1,2-b]pyridazine-3-carbonyl)-amino]-acetic acid a) 1-Amino-1H-pyrrole-2-carboxylic acid methyl ester To a stirred, ice/water cooled mixture of 1H-pyrrole-2-carboxylic acid methyl ester (425 mg, 3.40 mmol) in NMP (10 mL) was added a solution of potassium tert-pentoxide in toluene (2.30 mL, 3.90 mmol, 25 wt % solution); then the solid of O-4-chlorobenzoyl hydroxyamine (670 mg, prepared according to the literature: Parlanti, L Discordia, R. P.; Hynes, J. Jr.; Miller, M. M.; O'Grady, H. R.; Shi, Z. *Org. Lett.* 2007, 9(19) 3821-3824) was added in one portion; the cold bath was removed after addition completed, and the slurry was stirred at rt for 30 min. Subsequently, the reaction was quenched by addition of saturate sodium bicarbonate solution, then extracted with EtOAc, washed with brine; organic layers was dried over anhydrous sodium sulfate, filtered, concentrated and the residue was column purified to give the desired product (309 mg). $^1$H NMR (CDCl$_3$, δ in ppm): 6.94 (t, 1H, J=2.3 Hz), 6.81 (dd, 1H, J=2.0 Hz, 4.0 Hz), 6.00 (dd, J=2.7 Hz, 4.3 Hz), 5.53 (br, s, 2H), 3.82 (s, 3H).

b) 1-tert-Butoxycarbonylamino-1H-pyrrole-2-carboxylic acid methyl ester

A mixture of 1-amino-1H-pyrrole-2-carboxylic acid methyl ester (309 mg, 2.20 mmol) and Boc$_2$O (577 mg, 2.64 mmol) in dioxane (10 mL) was refluxed for 12 h; then cooled, concentrated, the residue was directly purified with silica gel column to give the desired product (448 mg) as white solid. $^1$H NMR (CDCl$_3$, δ in ppm): 7.59 (s, br, 1H), 6.96-6.88 (m, 2H), 6.11 (dd, 1H, J=2.8 Hz, J=4.2 Hz), 3.80 (s, 3H), 1.49 (s, 9H).

c) 1-(Benzyl-tert-butoxycarbonyl-amino)-1H-pyrrole-2-carboxylic acid methyl ester Sodium hydride (105 mg, 2.24 mmol, 60% purity in mineral oil) was added in one portion to a stirred, ice/water-cooled solution of 1-tert-butoxycarbonylamino-1H-pyrrole-2-carboxylic acid methyl ester (448 mg, 1.86 mmol) and benzyl bromide (267 µL, 2.24 mmol) in DMF (8 mL); the mixture was stirred in the cold bath for 60 min, at which time TLC showed complete disappearance of starting material; then poured into diluted, cold ammonium chloride solution to quench, followed by extraction with EtOAc, then washed with water, and brine; the organic phase was dried over anhydrous sodium sulfate, filtered, concentrated, and the residue was silica gel column purified to give the desired product (530 mg) as a clear oil. ESI (m/z): 353 (M+Na)$^+$.

d) 1-(Benzyl-tert-butoxycarbonyl-amino)-3,4,5-trichloro-1H-pyrrole-2-carboxylic acid methyl ester A mixture of 1-(benzyl-tert-butoxycarbonyl-amino)-1H-pyrrole-2-carboxylic acid methyl ester (530 mg, 1.60 mmol) and N-chlorosuccinimide (NCS) (750 mg, 5.61 mmol) in DMF (8 mL) was stirred in a 90° C. oil bath for 1 h; then the reaction mixture was cooled, diluted with EtOAc, washed with diluted sodium bicarbonate, water and brine respectively; subsequently, the organic layers was dried over anhydrous sodium sulfate, filtered, concentrated and purified with silica gel column to give the desired product (509 mg). ESI (m/z): 434 (M+H)$^+$. NMR showed existence of multiple rotamers.

e) 1-Benzylamino-3,4,5-trichloro-1H-pyrrole-2-carboxylic acid methyl ester 1-(Benzyl-tert-butoxycarbonyl-amino)-3,4,5-trichloro-1H-pyrrole-2-carboxylic acid methyl ester (509 mg, 1.17 mmol) was stirred in a mixture of dichloromethane (5 mL) and TFA (5 mL) at rt for 30 m in; then concentrated, the residue was dissolved in EtOAc, washed with diluted sodium bicarbonate, and saturated NaCl solution, dried over sodium sulfate, filtered, concentrated to give the crude product (394 mg) as white solid. ESI (m/z): 334 (M+H)$^+$.

f) 1-[Benzyl-(2-ethoxycarbonyl-acetyl)-amino]-3,4,5-trichloro-1H-pyrrole-2-carboxylic acid methyl ester A mixture of 1-benzylamino-3,4,5-trichloro-1H-pyrrole-2-carboxylic acid methyl ester (394 mg, 1.18 mmol) and chlorocarbonyl-acetic acid ethyl ester (227 μL, 1.77 mmol) in dioxane (5 mL) was stirred under reflux for 30 min; then the reaction mixture was cooled and the solvents were removed, the residue was directly silica gel column purified to give the desired product (278 mg) as colorless syrup. ESI (m/z): 447 $(M+H)^+$.

g) 1-Benzyl-5,6,7-trichloro-4-hydroxy-2-oxo-1,2-dihydro-pyrrolo[1,2-b]pyridazine-3-carboxylic acid methyl ester A mixture of 1-[benzyl-(2-ethoxycarbonyl-acetyl)-amino]-3,4,5-trichloro-1H-pyrrole-2-carboxylic acid methyl ester (278 mg, 0.62 mmol) and NaOMe in MeOH (5 mL, 2.5 mmol) in MeOH (3 mL) was refluxed for 4 h; then cooled, the reaction mixture was poured into ice cold 0.5 M HCl solution to quench, the precipitates were collected by filtration and then purified with silica gel column to give the desired product (85 mg) as slightly yellow solid. ESI (m/z): 401 $(M+H)^+$.

h) [(1-Benzyl-5,6,7-trichloro-4-hydroxy-2-oxo-1,2-dihydro-pyrrolo[1,2-b]pyridazine-3-carbonyl)-amino]-acetic acid Prepared according to the glycinolysis condition used in Example 1 step d). ESI (m/z): 444 $(M+H)^+$.

Example 3

{[1-(4-Fluoro-benzyl)-4-hydroxy-2-oxo-1,2-dihydro-pyrrolo[1,2-b]pyridazine-3-carbonyl]-amino}-acetic acid a) (4-Fluoro-benzyl)-pyrrol-1-yl-carbamic acid tert-butyl ester

Prepared according to the benzylation condition used in Example 1 step b) from pyrrol-1-yl-carbamic acid tert-butyl ester (1.0 eq.), 4-fluorobenzyl bromide (1.2 eq.) and sodium hydride (1.5 eq.). ESI (m/z): 291 $(M+H)^+$.

b) 1-(4-Fluoro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (4-fluoro-benzyl)-pyrrol-1-yl-carbamic acid tert-butyl ester (1.0 eq.) and 2-ethoxycarbonyl-malonic acid diethyl ester (2.0 eq.). ESI (m/z): 331 $(M+H)^+$.

c) {[1-(4-Fluoro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(4-fluoro-benzyl)-4-hydroxy-2-oxo-1,2-dihydro-pyrrolo[1,2-b]pyridazine-3-carboxylic acid ethyl ester and sodium glycinate. ESI (m/z): 360 $(M+H)^+$.

Example 4

[(4-Hydroxy-2-oxo-1,2-dihydro-pyrrolo[1,2-b]pyridazine-3-carbonyl)-amino]-acetic acid a) 4-Hydroxy-2-oxo-1,2-dihydro-pyrrolo[1,2-b]pyridazine-3-carboxylic acid ethyl ester A mixture of N-aminopyrrole (1.77 g, 20.56 mmol) and 2-ethoxycarbonyl-malonic acid diethyl ester (14.4 g, 61.68 mmol) was subjected microwave heating at 170° C. for 30 min; then cooled, the reaction mixture was directly purified with silica gel column to give the desired product (372 mg) as brown solid. ESI (m/z): 223 $(M+H)^+$.

b) [(4-Hydroxy-2-oxo-1,2-dihydro-pyrrolo[1,2-b]pyridazine-3-carbonyl)-amino]-acetic acid Prepared according to the glycinolysis condition used in Example 1 step d) from 4-hydroxy-2-oxo-1,2-dihydro-pyrrolo[1,2-b]pyridazine-3-carboxylic acid ethyl ester (1.0 eq.) and sodium glycinate (15 eq.) in 2-methoxyethanol. ESI (m/z): 252 $(M+H)^+$.

Example 5

{[1-(2-Fluoro-benzyl)-4-hydroxy-2-oxo-1,2-dihydro-pyrrolo[1,2-b]pyridazine-3-carbonyl]-amino}-acetic acid a) (2-Fluoro-benzyl)-pyrrol-1-yl-carbamic acid tert-butyl ester

Prepared according to the benzylation condition used in Example 1 step b) from pyrrol-1-yl-carbamic acid tert-butyl ester (1.0 eq.), 2-fluorobenzyl chloride (1.2 eq.) and sodium hydride (1.3 eq.). ESI (m/z): 291 $(M+H)^+$.

b) 1-(2-Fluoro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (2-fluoro-benzyl)-pyrrol-1-yl-carbamic acid tert-butyl ester (1.0 eq.) and 2-ethoxycarbonyl-malonic acid diethyl ester (3.0 eq.). ESI (m/z): 331 $(M+H)^+$.

c) {[1-(2-Fluoro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(2-fluoro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 360 $(M+H)^+$.

Example 6

{[1-(2,4-Difluoro-benzyl)-4-hydroxy-2-oxo-1,2-dihydro-pyrrolo[1,2-b]pyridazine-3-carbonyl]-amino}-acetic acid a) (2,4-Difluoro-benzyl)-pyrrol-1-yl-carbamic acid tert-butyl ester

Prepared according to the benzylation condition used in Example 1 step b) from pyrrol-1-yl-carbamic acid tert-butyl ester (1.0 eq.), 2,4-difluorobenzyl bromide (1.03 eq.) and sodium hydride (1.3 eq.). ESI (m/z): 309 (M+H)$^+$.

b) 1-(2,4-Difluoro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (2,4-difluoro-benzyl)-pyrrol-1-yl-carbamic acid tert-butyl ester (1.0 eq.) and 2-ethoxycarbonyl-malonic acid diethyl ester (3.0 eq.). ESI (m/z): 349 (M+H)$^+$.

c) {[1-(2,4-Difluoro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(2,4-difluoro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 378 (M+H)$^+$.

Example 7

{[1-(2-Chloro-benzyl)-4-hydroxy-2-oxo-1,2-dihydro-pyrrolo[1,2-b]pyridazine-3-carbonyl]-amino}-acetic acid a) (2-Chloro-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 2-chlorobenzyl chloride (1.03 eq.) and sodium hydride (1.3 eq.). ESI (m/z): 307 (M+H)$^+$.

b) 1-(2-Chloro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (2-chloro-benzyl)-pyrrol-1-yl-carbamic acid tert-butyl ester (1.0 eq.) and 2-ethoxycarbonyl-malonic acid diethyl ester (3.0 eq.). ESI (m/z): 347 (M+H)$^+$.

c) {[1-(2-Chloro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(2-chloro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 376 (M+H)$^+$.

Example 8

{[1-(3-Chloro-benzyl)-4-hydroxy-2-oxo-1,2-dihydro-pyrrolo[1,2-b]pyridazine-3-carbonyl]-amino}-acetic acid a) (3-Chloro-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 3-chlorobenzyl chloride (1.03 eq.) and sodium hydride (1.3 eq.). ESI (m/z): 307 (M+H)$^+$.

b) 1-(3-Chloro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (3-chloro-benzyl)-pyrrol-1-yl-carbamic acid tert-butyl ester (1.0 eq.) and 2-ethoxycarbonyl-malonic acid diethyl ester (3.0 eq.). ESI (m/z): 347 (M+H)$^+$.

c) {[1-(3-Chloro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(3-chloro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 376 (M+H)$^+$.

Example 9

[(4-Hydroxy-1-naphthalen-2-ylmethyl-2-oxo-1,2-dihydro-pyrrolo[1,2-b]pyridazine-3-carbonyl)-amino]-acetic acid a) Naphthalen-2-ylmethyl-pyrrol-1-yl-carbamic acid tert-butyl ester Prepared according to the benzylation condition used in Example 1 step b) from pyrrol-1-yl-carbamic acid tert-butyl ester (1.0 eq.), 2-bromomethyl-naphthalene (1.03 eq.) and sodium hydride (1.3 eq.). ESI (m/z): 323 (M+H)$^+$.

b) 4-Hydroxy-1-naphthalen-2-ylmethyl-2-oxo-1,2-dihydro-pyrrolo[1,2-b]pyridazine-3-carboxylic acid ethyl ester Prepared according to the thermal cyclization condition used in Example 1 step c) from naphthalen-2-ylmethyl-pyrrol-1-yl-carbamic acid tert-butyl ester (1.0 eq.) and 2-ethoxycarbonyl-malonic acid diethyl ester (3.0 eq.). ESI (m/z): 363 (M+H)$^+$.

c) [(4-Hydroxy-1-naphthalen-2-ylmethyl-2-oxo-1,2-dihydro-pyrrolo[1,2-b]pyridazine-3-carbonyl)-amino]-acetic acid Prepared according to the glycinolysis condition used in Example 1 step d) from 4-hydroxy-1-naphthalen-2-ylmethyl-2-oxo-1,2-dihydro-pyrrolo[1,2-b]pyridazine-3-carboxylic acid ethyl ester (1.0 eq.) and sodium glycinate (15 eq.). ESI (m/z): 392 (M+H)$^+$.

Example 10

{[1-(4-Trifluoromethyl-benzyl)-4-hydroxy-2-oxo-1,2-dihydro-pyrrolo[1,2-b]pyridazine-3-carbonyl]-amino}-acetic acid a) (4-Trifluoromethyl-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 4-trifluoromethylbenzyl chloride (1.0 eq.) and sodium hydride (1.3 eq.). ESI (m/z): 341 (M+H)$^+$.

b) 1-(4-Trifluoromethyl-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (4-trifluoromethyl-benzyl)-pyrrol-1-yl-carbamic acid tert-butyl ester (1.0 eq.) and 2-ethoxycarbonyl-malonic acid diethyl ester (3.0 eq.). ESI (m/z): 381 (M+H)$^+$.

c) {[1-(4-Trifluoromethyl-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(4-trifluoromethyl-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 410 (M+H)$^+$.

Example 11

{[1-(4-Chloro-benzyl)-4-hydroxy-2-oxo-1,2-dihydro-pyrrolo[1,2-b]pyridazine-3-carbonyl]-amino}-acetic acid a) (4-Chloro-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 4-chlorobenzyl chloride (1.03 eq.) and sodium hydride (1.3 eq.). ESI (m/z): 307 (M+H)$^+$.

b) 1-(4-Chloro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (4-chloro-benzyl)-pyrrol-1-yl-carbamic acid tert-butyl ester (1.0 eq.) and 2-ethoxycarbonyl-malonic acid diethyl ester (3.0 eq.). ESI (m/z): 347 (M+H)$^+$.

c) {[1-(4-Chloro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(4-chloro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 376 (M+H)$^+$.

Example 12

{[1-(4-Methoxy-benzyl)-4-hydroxy-2-oxo-1,2-dihydro-pyrrolo[1,2-b]pyridazine-3-carbonyl]-amino}-acetic acid a) (4-Methoxy-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 4-methoxybenzyl chloride (1.03 eq.) and sodium hydride (1.3 eq.). ESI (m/z): 303 (M+H)$^+$.

b) 1-(4-Methoxy-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (4-methoxy-benzyl)-pyrrol-1-yl-carbamic acid tert-butyl ester (1.0 eq.) and 2-ethoxycarbonyl-malonic acid diethyl ester (3.0 eq.). ESI (m/z): 343 (M+H)$^+$.

c) {[1-(4-Methoxy-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(4-methoxy-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 372 (M+H)$^+$.

Example 13

{[1-(3-Trifluoromethyl-benzyl)-4-hydroxy-2-oxo-1,2-dihydro-pyrrolo[1,2-b]pyridazine-3-carbonyl]-amino}-acetic acid a) (3-Trifluoromethyl-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 3-trifluoromethylbenzyl chloride (1.0 eq.) and sodium hydride (1.3 eq.). ESI (m/z): 341 (M+H)$^+$.

b) 1-(3-Trifluoromethyl-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from starting materials (3-trifluoromethyl-benzyl)-pyrrol-1-yl-carbamic acid tert-butyl ester (1.0 eq.) and 2-ethoxycarbonyl-malonic acid diethyl ester (3.0 eq.). ESI (m/z): 381 (M+H)$^+$.

c) {[1-(3-Trifluoromethyl-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(3-trifluoromethyl-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 410 (M+H)$^+$.

Example 14

{[1-(3-Fluoro-benzyl)-4-hydroxy-2-oxo-1,2-dihydro-pyrrolo[1,2-b]pyridazine-3-carbonyl]-amino}-acetic acid a) (3-Fluoro-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 3-fluorobenzyl bromide (1.0 eq.) and sodium hydride (1.3 eq.). ESI (m/z): 291 (M+H)⁺.

b) 1-(3-Fluoro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (3-fluoro-benzyl)-pyrrol-1-yl-carbamic acid tert-butyl ester (1.0 eq.) and 2-ethoxycarbonyl-malonic acid diethyl ester (3.0 eq.). ESI (m/z): 331 (M+H)⁺.

c) {[1-(3-Fluoro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(3-fluoro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 360 (M+H)⁺.

Example 15

{[1-(2,6-Difluoro-benzyl)-4-hydroxy-2-oxo-1,2-dihydro-pyrrolo[1,2-b]pyridazine-3-carbonyl]-amino}-acetic acid a) (2,6-Difluoro-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 2,6-difluorobenzyl chloride (1.0 eq.) and sodium hydride (1.3 eq.). ESI (m/z): 309 (M+H)⁺.

b) 1-(2,6-Difluoro-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (2,6-difluoro-benzyl)-pyrrol-1-yl-carbamic acid tert-butyl ester (1.0 eq.) and 2-ethoxycarbonyl-malonic acid diethyl ester (3.0 eq.). ESI (m/z): 349 (M+H)⁺.

c) {[1-(2,6-Difluoro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(2,6-difluoro-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 378 (M+H)⁺.

Example 16

{[1-(2-Trifluoromethyl-benzyl)-4-hydroxy-2-oxo-1,2-dihydro-pyrrolo[1,2-b]pyridazine-3-carbonyl]-amino}-acetic acid a) (2-Trifluoromethyl-benzyl)-pyrrol-1-yl-carbamic acid tert-butyl ester Prepared according to the benzylation condition used in Example 1 step b) from pyrrol-1-yl-carbamic acid tert-butyl ester (1.0 eq.), 2-trifluoromethylbenzyl chloride (1.0 eq.) and sodium hydride (1.3 eq.). ESI (m/z): 341 (M+H)⁺.

b) 1-(2-Trifluoromethyl-benzyl)-4-hydroxy-2-oxo-1,2-dihydro-pyrrolo[1,2-b]pyridazine-3-carboxylic acid ethyl ester Prepared according to the thermal cyclization condition used in Example 1 step c) from (2-trifluoromethyl-benzyl)-pyrrol-1-yl-carbamic acid tert-butyl ester (1.0 eq.) and 2-ethoxycarbonyl-malonic acid diethyl ester (3.0 eq.). ESI (m/z): 381 (M+H)⁺.

c) {[1-(2-Trifluoromethyl-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 1-(2-trifluoromethyl-benzyl)-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 410 (M+H)⁺.

Example 17

[(1-Butyl-4-hydroxy-2-oxo-1,2-dihydro-pyrrolo[1,2-b]pyridazine-3-carbonyl)-amino]-acetic acid a) Butyl-pyrrol-1-yl-carbamic acid tert-butyl ester Prepared according to the N-alkylation condition used in Example 1 step b) from starting materials pyrrol-1-yl-carbamic acid tert-butyl ester (1.0 eq.), 1-iodobutane (2.0 eq.) and sodium hydride (1.3 eq.). 1H NMR (CDCl₃, δ in ppm): 6.60 (m, 2H), 6.10 (m, 2H), 3.64 (t, 2H, J=7.0 Hz), 1.42 (s, 9H), 1.55-1.26 (m, 4H), 0.92 (t, 3H, J=7.0 Hz).

b) Butyl-pyrrol-1-yl-amine

A mixture of butyl-pyrrol-1-yl-carbamic acid tert-butyl ester (1.435 g), triethylamine (2.06 mL) and TMSOTf (1.79 mL) in DCM was stirred at rt for 15 min. The mixture was then diluted with DCM, washed with water, saturated sodium chloride solution and then dried over sodium sulfate, filtered, concentrated to give the desired product as oil (943 mg). ¹H NMR (CDCl₃, δ in ppm): 6.74 (m, 2H), 6.04 (m, 2H), 4.9 (very broad, 1H), 3.11 (t, 2H, J=7.1 Hz), 1.44-1.22 (m, 4H), 0.92 (t, 2H, J=7.3 Hz).

c) 1-Butyl-4-hydroxy-2-oxo-1,2-dihydro-pyrrolo[1,2-b]pyridazine-3-carboxylic acid ethyl ester A mixture of butyl-pyrrol-1-yl-amine (943 mg) and 2-ethoxycarbonyl-malonic acid diethyl ester (3.15 mL) in a test tube was heated for 30 min at 170° C. and then 30 min at 200° C.; then cooled, the residue was directly column-purified to give the desired product (778 mg) as brown liquid. ESI (m/z): 279 (M+H)⁺.

d) [(1-Butyl-4-hydroxy-2-oxo-1,2-dihydro-pyrrolo[1,2-b]pyridazine-3-carbonyl)-amino]-acetic acid Prepared according to the glycinolysis condition used in Example 1 step d) from 1-butyl-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 308 (M+H)⁺.

Example 18

{[4-(4-Fluoro-benzyl)-1-hydroxy-3-oxo-3,4-dihydro-4,4a-diaza-fluorene-2-carbonyl]-amino}-acetic acid

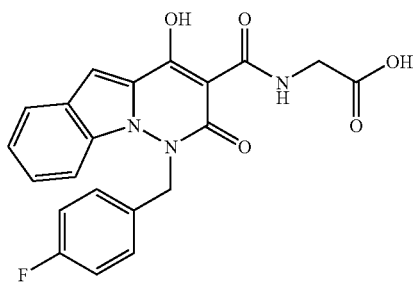

a) 1-Amino-1H-indole-2-carboxylic acid ethyl ester

To a mixture of 1H-indole-2-carboxylic acid ethyl ester (2.07 g, Sigma-Aldridch) in MTBE (25 mL) was added in the order of: ammonium chloride (2.96 g), ALIQUAT 336 (124 mg; Cognis Corp., Monheim, Germany), sodium hydroxide (7.44 g), concentrated ammonium hydroxide solution (4.06 mL); the resulting mixture was rigorously stirred at rt, then a 10% solution of NaOCl (67 mL) was added dropwise over a period of 30 min. The reaction was stirred for 3 h after addition of NaOCl, then diluted with EtOAc, washed with water and sat. NaCl solution respectively, dried over sodium sulfate, filtered, concentrated, then the residue was column-purified to give product (1.48 g) as slightly yellow oil. ¹H NMR (CDCl₃, δ in ppm): 7.65-7.58 (m, 2H), 7.35 (t, 1H, J=7.0 Hz), 7.18-7.11 (m, 2H), 6-4.5 (very broad, 2H), 4.38 (q, 2H, J=7.0 Hz), 1.42 (t, 3H, J=7.0 Hz).

b) 1-[(4-Fluoro-benzylidene)-amino]-1H-indole-2-carboxylic acid ethyl ester

A mixture of 1-amino-1H-indole-2-carboxylic acid ethyl ester (1.48 g) and 4-fluorobenzaldehyde (1.55 mL) in ethanol (20 mL) was refluxed for 1 h. TLC showed complete reaction, the mixture was directly used in the next step. An aliquot (20 micro liters) of the reaction mixture was taken and concentrated for the NMR analysis. ¹H NMR (CDCl₃, δ in ppm): 8.52 (s, 1H), 7.95 (m, 2H), 7.63 (m, 2H), 7.35 (m, 2H), 7.17 (m, 4H), 4.35 (q, 2H, J=7.0 Hz), 1.36 (t, 3H, J=7.0 Hz).

c) 1-(4-Fluoro-benzylamino)-1H-indole-2-carboxylic acid ethyl ester

The above reaction mixture was diluted with THF (20 mL) at rt, then sodium borohydride (1.37 g) was added, the reaction mixture was then refluxed for 1 h, by which time TLC showed complete reaction; then the reaction mixture was cooled, 2 mL HOAc was added to quench the reaction, extracted with EtOAc, washed with water (2 times) and sat. NaCl solution respectively, dried over anhydrous sodium sulfate, filtered and concentrated. The product was sufficiently pure and used directly in the next step. ESI (m/z): 313 (M+H)⁺.

d) 1-[(4-Fluoro-benzyl)-(2-methoxycarbonyl-acetyl)-amino]-1H-indole-2-carboxylic acid ethyl ester Prepared according to the acylation condition used in Example 2 step f) from 1-(4-fluoro-benzylamino)-1H-indole-2-carboxylic acid methyl ester (1.0 eq.) and chlorocarbonyl-acetic acid methyl ester (2.2 eq.). ESI (m/z): 413 (M+H)⁺.

e) 4-(4-Fluoro-benzyl)-1-hydroxy-3-oxo-3,4-dihydro-4,4a-diaza-fluorene-2-carboxylic acid methyl ester Prepared according to the cyclization condition used in Example 2 step g) from 1-[(4-fluoro-benzyl)-(2-methoxycarbonyl-acetyl)-amino]-1H-indole-2-carboxylic acid ethyl ester. ESI (m/z): 367 (M+H)⁺.

f) {[4-(4-Fluoro-benzyl)-1-hydroxy-3-oxo-3,4-dihydro-4,4a-diaza-fluorene-2-carbonyl]-amino}-acetic acid Prepared according to the glycinolysis condition used in Example 1 step d) from 4-(4-fluoro-benzyl)-1-hydroxy-3-oxo-3,4-dihydro-4,4a-diaza-fluorene-2-carboxylic acid methyl ester (1.0 eq.) and sodium glycinate (15 eq.). ESI (m/z): 410 (M+H)⁺.

Example 19

2-(S)-{[4-(4-Fluoro-benzyl)-1-hydroxy-3-oxo-3,4-dihydro-4,4a-diaza-fluorene-2-carbonyl]-amino}-propionic acid

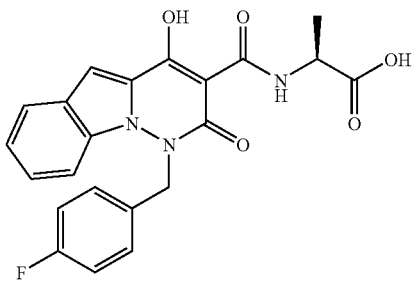

A mixture of 4-(4-fluoro-benzyl)-1-hydroxy-3-oxo-3,4-dihydro-4,4a-diaza-fluorene-2-carboxylic acid methyl ester (110 mg), L-alanine (268 mg), NaOMe (146 mg) in 2-methoxyethanol (10 mL) was refluxed for 6 h; subsequently, the reaction was cooled and solvent was removed by rotovaping; the residue was dissolved in water and then acidified with 2 M HCl solution; the precipitates were collected via filtration, washed with water, dried, and then purified with column (eluent: DCM/EtOAc, 10/1 (v/v), with 0.5% acetic acid) to give the desired product (78 mg). ESI (m/z): 424 (M+H)⁺.

Example 20

[(1-Hexyl-4-hydroxy-2-oxo-1,2-dihydro-pyrrolo[1,2-b]pyridazine-3-carbonyl)-amino]-acetic acid a) Hexyl-pyrrol-1-yl-carbamic acid tert-butyl ester Prepared according to the N-alkylation condition used in Example 17 step a) from starting materials pyrrol-1-yl-carbamic acid tert-butyl ester (1.0 eq.), 1-iodohexane (3.0 eq.) and sodium hydride (1.3 eq.). $^1$H NMR (CDCl$_3$, δ in ppm): 6.60 (m, 2H), 6.10 (m, 2H), 3.63 (t, 2H, J=7.2 Hz), 1.42 (s, 9H), 1.9-1.2 (m, 8H), 0.90 (m, 3H).

b) Hexyl-pyrrol-1-yl-amine

Prepared according to Boc-removing condition used in Example 17 step b) from starting materials hexyl-pyrrol-1-yl-carbamic acid tert-butyl ester, TMSOTf and triethylamine. $^1$H NMR (CDCl$_3$, δ in ppm): 6.75 (t, 2H, J=2.4 Hz), 6.04 (t, 2H, J=2.4 Hz), 6-4 (very broad, 1H), 3.11 (t, 2H, J=7.1 Hz), 1.6-1.2 (m, 8H), 0.88 (t, 3H, J=7.2 Hz).

c) 1-Hexyl-4-hydroxy-2-oxo-1,2-dihydro-pyrrolo[1,2-b]pyridazine-3-carboxylic acid ethyl ester Prepared according to the condition used in Example 17 step c) from hexyl-pyrrol-1-yl-amine. ESI (m/z): 307 (M+H)$^+$.

d) [(1-Hexyl-4-hydroxy-2-oxo-1,2-dihydro-pyrrolo[1,2-b]pyridazine-3-carbonyl)-amino]-acetic acid Prepared according to the glycinolysis condition used in Example 1 step d) from 1-hexyl-4-hydroxy-2-oxo-1,2-dihydro-pyrrolo[1,2-b]pyridazine-3-carboxylic acid ethyl ester (1.0 eq.) and sodium glycinate (15 eq.). ESI (m/z): 336 (M+H)$^+$.

Example 21

{[7-Fluoro-4-(4-fluoro-benzyl)-1-hydroxy-3-oxo-3,4-dihydro-4,4a-diaza-fluorene-2-carbonyl]-amino}-acetic acid

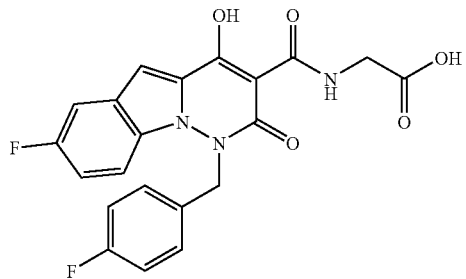

a) 1-Amino-5-fluoro-1H-indole-2-carboxylic acid ethyl ester

Prepared according to the N-amination condition used in Example 18 step a) from 5-fluoro-1H-indole-2-carboxylic acid ethyl ester (prepared according to literature: J. Chem. Soc. 1955, 1283-1284), ammonium chloride, ALIQUAT 336, sodium hydroxide, concentrated ammonium hydroxide solution and 10% solution of NaOCl. ESI (m/z): 223 (M+H)$^+$.

b) 5-Fluoro-1-[(4-fluoro-benzylidene)-amino]-1H-indole-2-carboxylic acid ethyl ester Prepared according to the imine formation condition used in Example 18 step b) from 1-amino-5-fluoro-1H-indole-2-carboxylic acid ethyl ester. $^1$H NMR (CDCl$_3$, δ in ppm): 8.50 (s, 1H), 7.90 (dd, 2H, J=5.2 Hz, 8.8 Hz), 7.55 (m, 1H), 7.34-7.09 (m, 5H), 4.34 (q, 2H, J=7.0 Hz), 1.35 (t, 3H, J=7.0 Hz).

c) 5-Fluoro-1-(4-fluoro-benzylamino)-1H-indole-2-carboxylic acid ethyl ester

Prepared according to the reduction condition used in Example 18 step c) from 5-fluoro-1-[(4-fluoro-benzylidene)-amino]-1H-indole-2-carboxylic acid ethyl ester. ESI (m/z): 331 (M+H)$^+$.

d) 5-Fluoro-1-[(4-fluoro-benzyl)-(2-methoxycarbonyl-acetyl)-amino]-1H-indole-2-carboxylic acid ethyl ester Prepared according to the acylation condition used in Example 2 step f) from 5-fluoro-1-(4-fluoro-benzylamino)-1H-indole-2-carboxylic acid ethyl ester and chlorocarbonyl-acetic acid methyl ester (1.2 eq.). $^1$H NMR (CDCl$_3$, δ in ppm): 7.3-6.77 (m, 8H), 4.82 (dd, 2H), 4.17 (m, 2H), 3.54 (s, 3H), 3.26 (s, 2H), 1.31 (t, 3H, J=7.1 Hz).

e) 7-Fluoro-4-(4-fluoro-benzyl)-1-hydroxy-3-oxo-3,4-dihydro-4,4a-diaza-fluorene-2-carboxylic acid methyl ester Prepared according to the cyclization condition used in Example 2 step g) from 5-fluoro-1-[(4-fluoro-benzyl)-(2-methoxycarbonyl-acetyl)-amino]-1H-indole-2-carboxylic acid ethyl ester. $^1$H NMR (DMSO-d6, δ in ppm): 14.0 (s, 1H), 7.5-6.6 (m, 8H), 5.55 (s, 2H), 4.01 (s, 3H).

f) {[7-Fluoro-4-(4-fluoro-benzyl)-1-hydroxy-3-oxo-3,4-dihydro-4,4a-diaza-fluorene-2-carbonyl]-amino}-acetic acid Prepared according to the glycinolysis condition used in Example 1 step d) from 7-fluoro-4-(4-fluoro-benzyl)-1-hydroxy-3-oxo-3,4-dihydro-4,4a-diaza-fluorene-2-carboxylic acid methyl ester (1.0 eq.) and sodium glycinate (15 eq.). ESI (m/z): 428 (M+H)$^+$.

Example 22

{[6-Chloro-4-hydroxy-2-oxo-1-(4-trifluoromethyl-benzyl)-1,2-dihydro-pyrrolo[1,2-b]pyridazine-3-carbonyl]-amino}-acetic acid a) 4-Chloro-1-[(4-trifluoromethyl-benzylidene)-amino]-1H-pyrrole-2-carboxylic acid methyl ester Prepared according to the imine formation condition used in Example 18 step b) from 1-amino-4-chloro-1H-pyrrole-2-carboxylic acid methyl ester (prepared according to literature: *Bioorg & Med. Chem. Lett.* 2006, 16, 3937-3942) and 4-trifluoromethylbenzaldehyde in refluxing methanol for 12 h. $^1$H NMR (CDCl$_3$, δ in ppm): 8.43 (s, 1H), 7.95 (d, 2H, J=8.4 Hz), 7.70 (d, 2H, J=7.9 Hz), 7.23 (d, 1H, J=1.6 Hz), 6.91 (d, 1H, J=2.2 Hz), 3.84 (s, 3H).

b) 4-Chloro-1-(4-trifluoromethyl-benzylamino)-1H-pyrrole-2-carboxylic acid methyl ester Prepared according to the reduction condition used in Example 18 step c) from 4-chloro-1-[(4-trifluoromethyl-benzylidene)-amino]-1H-pyrrole-2-carboxylic acid methyl ester. ¹H NMR (CDCl₃, δ in ppm): 7.58 (d, 2H, J=8 Hz), 7.39 (d, 2H, J=8 Hz), 6.73 (s, 2H), 7.6-5.4 (very broad, 1H), 4.14 (s, 2H), 3.81 (s, 3H).

c) 4-Chloro-1-[(2-methoxycarbonyl-acetyl)-(4-trifluoromethyl-benzyl)-amino]-1H-pyrrole-2-carboxylic acid methyl ester Prepared according to the acylation condition used in Example 2 step f) from 4-chloro-1-(4-trifluoromethyl-benzylamino)-1H-pyrrole-2-carboxylic acid methyl ester and chlorocarbonylacetic acid methyl ester (1.5 eq.). ¹H NMR (CDCl₃, δ in ppm): 7.56 (d, 2H, J=8.0 Hz), 7.30 (d, 2H, J=8.0 Hz), 6.84 (d, 1H, J=2.2 Hz), 6.52 (d, 2H, J=2.2 Hz), 5.31 (d, 1H, J=14.6 Hz), 4.48 (d, 1H, J=15.0 Hz), 3.73 (s, 3H), 3.72 (s, 3H), 3.20 (dd, 3H, J=14.6 Hz, 16.2 Hz).

d) 6-Chloro-4-hydroxy-2-oxo-1-(4-trifluoromethyl-benzyl)-1,2-dihydro-pyrrolo[1,2-b]pyridazine-3-carboxylic acid methyl ester Prepared according to the cyclization condition used in Example 2 step g) from 4-Chloro-1-[(2-methoxycarbonyl-acetyl)-(4-trifluoromethyl-benzyl)-amino]-1H-pyrrole-2-carboxylic acid methyl ester. ¹H NMR (CDCl₃, δ in ppm): 14.09 (s, 1H), 7.61 (d, 2H, J=8.0 Hz), 7.40 (d, 2H, J=8.0 Hz), 6.93 (d, 1H, J=2.2 Hz), 6.86 (d, 1H, J=2.2 Hz), 5.50 (s, 2H), 4.02 (s, 3H).

e) {[6-Chloro-4-hydroxy-2-oxo-1-(4-trifluoromethyl-benzyl)-1,2-dihydro-pyrrolo[1,2-b]pyridazine-3-carbonyl]-amino}-acetic acid Prepared according to the glycinolysis condition used in Example 1 step d) from 6-chloro-4-hydroxy-2-oxo-1-(4-trifluoromethyl-benzyl)-1,2-dihydro-pyrrolo[1,2-b]pyridazine-3-carboxylic acid methyl ester (1.0 eq.) and sodium glycinate (15 eq.). ESI (m/z): 444 (M+H)⁺.

Example 23

2-(S)-{[6-Chloro-4-hydroxy-2-oxo-1-(4-trifluoromethyl-benzyl)-1,2-dihydro-pyrrolo[1,2-b]pyridazine-3-carbonyl]-amino}-propionic acid Prepared according to the reaction condition used in Example 19 step a) from 6-chloro-4-hydroxy-2-oxo-1-(4-trifluoromethyl-benzyl)-1,2-dihydro-pyrrolo[1,2-b]pyridazine-3-carboxylic acid methyl ester, L-alanine and NaOMe. ESI (m/z): 458 (M+H)⁺.

Example 24

2-(S)-{[4-Hydroxy-2-oxo-1-(4-trifluoromethyl-benzyl)-1,2-dihydro-pyrrolo[1,2-b]pyridazine-3-carbonyl]-amino}-propionic acid Prepared according to the reaction condition used in Example 19 step a) from 4-hydroxy-2-oxo-1-(4-trifluoromethyl-benzyl)-1,2-dihydro-pyrrolo[1,2-b]pyridazine-3-carboxylic acid methyl ester, L-alanine and NaOMe. ESI (m/z): 424 (M+H)⁺.

Example 25

2-(S)-{[4-Hydroxy-2-oxo-1-(4-trifluoromethyl-benzyl)-1,2-dihydro-pyrrolo[1,2-b]pyridazine-3-carbonyl]-amino}-butyric acid Prepared according to the reaction condition used in Example 19 step a) from 4-hydroxy-2-oxo-1-(4-trifluoromethyl-benzyl)-1,2-dihydro-pyrrolo[1,2-b]pyridazine-3-carboxylic acid methyl ester, L-2-aminobutyric acid and NaOMe. ESI (m/z): 438 (M+H)⁺.

Example 26

{[6-Chloro-4-hydroxy-2-oxo-1-(4-fluoro-benzyl)-1,2-dihydro-pyrrolo[1,2-b]pyridazine-3-carbonyl]-amino}-acetic acid a) 4-Chloro-1-[(4-fluoro-benzylidene)-amino]-1H-pyrrole-2-carboxylic acid methyl ester Prepared according to the imine formation condition used in Example 18 step b) from 1-amino-4-chloro-1H-pyrrole-2-carboxylic acid methyl ester and 4-fluoro benzaldehyde in refluxing methanol for 12 h. ESI (m/z): 281 (M+H)⁺.

b) 4-Chloro-1-(4-fluoro-benzylamino)-1H-pyrrole-2-carboxylic acid methyl ester

Prepared according to the reduction condition used in Example 18 step c) from 4-chloro-1-[(4-fluoro-benzylidene)-amino]-1H-pyrrole-2-carboxylic acid methyl ester. ESI (m/z): 283 (M+H)⁺.

c) 4-Chloro-1-[(2-methoxycarbonyl-acetyl)-(4-fluoro-benzyl)-amino]-4-1H-pyrrole-2-carboxylic acid methyl ester Prepared according to the acylation condition used in Example 2 step f) from 4-chloro-1-(4-fluoro-benzylamino)-1H-pyrrole-2-carboxylic acid methyl ester and chlorocarbonyl-acetic acid methyl ester (1.5 eq.). ESI (m/z): 383 (M+H)⁺.

d) 6-Chloro-4-hydroxy-2-oxo-1-(4-fluoro-benzyl)-1,2-dihydro-pyrrolo[1,2-b]pyridazine-3-carboxylic acid methyl ester Prepared according to the cyclization condition used in Example 2 step g) from 4-chloro-1-[(2-methoxycarbonyl-acetyl)-(4-fluoro-benzyl)-amino]-1H-pyrrole-2-carboxylic acid methyl ester. ESI (m/z): 351 (M+H)⁺.

e) {[6-Chloro-4-hydroxy-2-oxo-1-(4-fluoro-benzyl)-1,2-dihydro-pyrrolo[1,2-b]pyridazine-3-carbonyl]-amino}-acetic acid Prepared according to the glycinolysis condition used in Example 1 step d) from 6-chloro-4-hydroxy-2-oxo-1-(4-fluoro-benzyl)-1,2-dihydro-pyrrolo[1,2-b]pyridazine-3-carboxylic acid methyl ester (1.0 eq.) and sodium glycinate (15 eq.). ESI (m/z): 394 (M+H)⁺.

Example 27

2-(S)-{[6-Chloro-1-(4-fluoro-benzyl)-4-hydroxy-2-oxo-1,2-dihydro-pyrrolo[1,2-b]pyridazine-3-carbonyl]-amino}-propionic acid Prepared according to the reaction condition used in Example 19 step a) from 6-chloro-4-hydroxy-2-oxo-1-(4- fluoro-benzyl)-1,2-dihydro-pyrrolo[1,2-b]pyridazine-3-carboxylic acid methyl ester, L-alanine and NaOMe. ESI (m/z): 408 (M+H)$^+$.

Example 28

{[6-Chloro-1-(4-chloro-benzyl)-4-hydroxy-2-oxo-1,2-dihydro-pyrrolo[1,2-b]pyridazine-3-carbonyl]-amino}-acetic acid a) 4-Chloro-1-[(4-chloro-benzylidene)-amino]-1H-pyrrole-2-carboxylic acid methyl ester Prepared according to the imine formation condition used in Example 18 step b) from 1-amino-4-chloro-1H-pyrrole-2-carboxylic acid methyl ester and 4-chloro benzaldehyde in refluxing methanol for 12 h. $^1$H NMR (CDCl$_3$, δ in ppm): 8.35 (s, 1H), 7.78 (d, 2H, J=7.6 Hz), 7.42 (d, 2H, J=7.6 Hz), 7.19 (d, 1H, J=2.2 Hz), 6.89 (d, 1H, J=2.2 Hz), 3.83 (s, 3H).

b) 4-Chloro-1-(4-chloro-benzylamino)-1H-pyrrole-2-carboxylic acid methyl ester Prepared according to the reduction condition used in Example 18 step c) from 4-chloro-1-[(4-chloro-benzylidene)-amino]-1H-pyrrole-2-carboxylic acid methyl ester. ESI (m/z): 299 (M+H)$^+$.

c) 4-Chloro-1-[(2-methoxycarbonyl-acetyl)-(4-chloro-benzyl)-amino]-1H-pyrrole-2-carboxylic acid methyl ester Prepared according to the acylation condition used in Example 2 step f) from 4-chloro-1-(4-chloro-benzylamino)-1H-pyrrole-2-carboxylic acid methyl ester and chlorocarbonyl-acetic acid methyl ester (1.5 eq.). $^1$H NMR (CDCl$_3$, δ in ppm): 7.26 (d, 2H, J=8.2 Hz), 7.08 (d, 2H, J=8.8 Hz), 6.83 (d, 1H, J=2.2 Hz), 6.47 (d, 1H, J=1.8 Hz), 5.27 (d, 1H, J=14.6 Hz), 4.27 (d, 1H, J=14.6 Hz), 3.75 (s, 3H), 3.69 (s, 3H), 3.18 (m, 2H).

d) 6-Chloro-4-hydroxy-2-oxo-1-(4-chloro-benzyl)-1,2-dihydro-pyrrolo[1,2-b]pyridazine-3-carboxylic acid methyl ester Prepared according to the cyclization condition used in Example 2 step g) from 4-chloro-1-[(2-methoxycarbonyl-acetyl)-(4-chloro-benzyl)-amino]-1H-pyrrole-2-carboxylic acid methyl ester. $^1$H NMR (CDCl$_3$, δ in ppm): 14.1 (s, 1H), 7.32 (d, 2H, J=8.4 Hz), 7.22 (d, 2H, J=8.4 Hz), 6.95 (d, 1H, J=1.8 Hz), 6.85 (d, 1H, J=2.2 Hz), 5.41 (s, 2H), 4.02 (s, 3H).

e) {[6-Chloro-4-hydroxy-2-oxo-1-(4-chloro-benzyl)-1,2-dihydro-pyrrolo[1,2-b]pyridazine-3-carbonyl]-amino}-acetic acid Prepared according to the glycinolysis condition used in Example 1 step d) from 6-chloro-4-hydroxy-2-oxo-1-(4-chloro-benzyl)-1,2-dihydro-pyrrolo[1,2-b]pyridazine-3-carboxylic acid methyl ester (1.0 eq.) and sodium glycinate (15 eq.). ESI (m/z): 410 (M+H)$^+$.

Example 29

2-(S)-{[6-Chloro-1-(4-chloro-benzyl)-4-hydroxy-2-oxo-1,2-dihydro-pyrrolo[1,2-b]pyridazine-3-carbonyl]-amino}-propionic acid Prepared according to the reaction condition used in Example 19 step a) from 6-chloro-4-hydroxy-2-oxo-1-(4-chloro-benzyl)-1,2-dihydro-pyrrolo[1,2-b]pyridazine-3-carboxylic acid methyl ester, L-alanine and NaOMe. ESI (m/z): 424 (M+H)$^+$.

Example 30

2-(S)-{[6-Chloro-1-(4-chloro-benzyl)-4-hydroxy-2-oxo-1,2-dihydro-pyrrolo[1,2-b]pyridazine-3-carbonyl]-amino}-butyric acid Prepared according to the reaction condition used in Example 19 step a) from 6-chloro-4-hydroxy-2-oxo-1-(4-chloro-benzyl)-1,2-dihydro-pyrrolo[1,2-b]pyridazine-3-carboxylic acid methyl ester, 2-L-amino butyric acid and NaOMe. ESI (m/z): 438 (M+H)$^+$.

Example 31

{[6-Chloro-1-(4-methoxy-benzyl)-4-hydroxy-2-oxo-1,2-dihydro-pyrrolo[1,2-b]pyridazine-3-carbonyl]-amino}-acetic acid a) 4-Chloro-1-[(4-methoxy-benzylidene)-amino]-1H-pyrrole-2-carboxylic acid methyl ester Prepared according to the imine formation condition used in Example 18 step b) from 1-amino-4-chloro-1H-pyrrole-2-carboxylic acid methyl ester and 4-methoxy benzaldehyde in refluxing methanol for 12 h. $^1$H NMR (CDCl$_3$, δ in ppm): 8.33 (s, 1H), 7.78 (d, 2H, J=8.8 Hz), 7.13 (d, 1H, J=2.2 Hz), 6.96 (d, 2H, J=8.8 Hz), 6.87 (d, 1H, J=1.8 Hz), 3.87 (s, 3H), 3.82 (s, 3H).

b) 4-Chloro-1-(4-methoxy-benzylamino)-1H-pyrrole-2-carboxylic acid methyl ester Prepared according to the reduction condition used in Example 18 step c) from 4-chloro-1-[(4-methoxy-benzylidene)-amino]-1H-pyrrole-2-carboxylic acid methyl ester. $^1$H NMR (CDCl$_3$, δ in ppm): 7.18 (d, 2H, J=8.4 Hz), 6.84 (d, 2H, J=8.2 Hz), 6.73 (s, 2H), 4.02 (s, 3H), 3.82 (s, 3H), 3.80 (s, 3H).

c) 4-Chloro-1-[(2-methoxycarbonyl-acetyl)-(4-methoxy-benzyl)-amino]-1H-pyrrole-2-carboxylic acid methyl ester Prepared according to the acylation condition used in Example 2 step f) from 4-chloro-1-(4-methoxy-benzylamino)-1H-pyrrole-2-carboxylic acid methyl ester and chlorocarbonyl-acetic acid methyl ester (1.5 eq.). ESI (m/z): 395 (M+H)$^+$.

d) 6-Chloro-4-hydroxy-2-oxo-1-(4-methoxy-benzyl)-1,2-dihydro-pyrrolo[1,2-b]pyridazine-3-carboxylic acid methyl ester Prepared according to the cyclization condition used in Example 2 step g) from 4-chloro-1-[(2-methoxycarbonyl-acetyl)-(4-methoxy-benzyl)-amino]-1H-pyrrole-2-carboxylic acid methyl ester. $^1$H NMR (CDCl$_3$, δ in ppm): 14.0 (s, 1H), 7.22 (d, 2H, J=8.4 Hz), 7.04 (d, 1H, J=1.8 Hz), 6.89-6.81 (m, 3H), 5.39 (s, 2H), 4.02 (s, 3H), 3.79 (s, 3H).

e) {[6-Chloro-4-hydroxy-2-oxo-1-(4-methoxy-benzyl)-1,2-dihydro-pyrrolo[1,2-b]pyridazine-3-carbonyl]-amino}-acetic acid Prepared according to the glycinolysis condition used in Example 1 step d) from 6-chloro-4-hydroxy-2-oxo-1-(4- methoxy-benzyl)-1,2-dihydro-pyrrolo[1,2-b]pyridazine-3-carboxylic acid methyl ester (1.0 eq.) and sodium glycinate (15 eq.). ESI (m/z): 406 (M+H)⁺.

Example 32

2-(S)-{[6-Chloro-1-(4-methoxy-benzyl)-4-hydroxy-2-oxo-1,2-dihydro-pyrrolo[1,2-b]pyridazine-3-carbonyl]-amino}-propionic acid Prepared according to the reaction condition used in Example 19 step a) from 6-chloro-4-hydroxy-2-oxo-1-(4-methoxy-benzyl)-1,2-dihydro-pyrrolo[1,2-b]pyridazine-3-carboxylic acid methyl ester, L-alanine and NaOMe. ESI (m/z): 420 (M+H)⁺.

Example 33

2-(S)-{[6-Chloro-1-(4-methoxy-benzyl)-4-hydroxy-2-oxo-1,2-dihydro-pyrrolo[1,2-b]pyridazine-3-carbonyl]-amino}-butyric acid Prepared according to the reaction condition used in Example 19 step a) from 6-chloro-4-hydroxy-2-oxo-1-(4-methoxy-benzyl)-1,2-dihydro-pyrrolo[1,2-b]pyridazine-3-carboxylic acid methyl ester, 2-L-amino butyric acid and NaOMe. ESI (m/z): 434 (M+H)⁺.

Example 34

2-(S)-{[6-Chloro-1-(4-fluoro-benzyl)-4-hydroxy-2-oxo-1,2-dihydro-pyrrolo[1,2-b]pyridazine-3-carbonyl]-amino}-butyric acid Prepared according to the reaction condition used in Example 19 step a) from 6-chloro-4-hydroxy-2-oxo-1-(4-fluoro-benzyl)-1,2-dihydro-pyrrolo[1,2-b]pyridazine-3-carboxylic acid methyl ester, 2-L-amino butyric acid and NaOMe. ESI (m/z): 422 (M+H)⁺.

Example 35

2-(S)-[(1-Biphenyl-4-ylmethyl-6-chloro-4-hydroxy-2-oxo-1,2-dihydro-pyrrolo[1,2-b]pyridazine-3-carbonyl)-amino]-propionic acid a) 1-[(Biphenyl-4-ylmethylene)-amino]-4-chloro-1H-pyrrole-2-carboxylic acid methyl ester Prepared according to the imine formation condition used in Example 18 step b) from 1-amino-4-chloro-1H-pyrrole-2-carboxylic acid methyl ester and 4-phenyl benzaldehyde in refluxing methanol for 12 h. ¹H NMR (CDCl₃, δ in ppm): 8.43 (s, 1H), 7.91 (d, 2H, J=8.4 Hz), 7.68 (d, 2H, J=8.4 Hz), 7.66-7.16 (m, 5H), 7.20 (d, 1H, J=2.2 Hz), 6.90 (d, 1H, J=1.8 Hz), 3.84 (s, 3H).

b) 1-[(Biphenyl-4-ylmethyl)-amino]-4-chloro-1H-pyrrole-2-carboxylic acid methyl ester Prepared according to the reduction condition used in Example 18 step c) from 1-[(biphenyl-4-ylmethylene)-amino]-4-chloro-1H-pyrrole-2-carboxylic acid methyl ester. ¹H NMR (CDCl₃, δ in ppm): 7.6-7.2 (m, 9H), 6.75 (m, 2H), 6.6 (broad, 1H), 4.12 (s, 2H), 3.82 (s, 3H).

c) 1-[Biphenyl-4-ylmethyl-(2-methoxycarbonyl-acetyl)-amino]-4-chloro-1H-pyrrole-2-carboxylic acid methyl ester Prepared according to the acylation condition used in Example 2 step f) from 1-[(biphenyl-4-ylmethyl)-amino]-4-chloro-1H-pyrrole-2-carboxylic acid methyl ester and chlorocarbonyl-acetic acid methyl ester (1.5 eq.). ESI (m/z): 441 (M+H)⁺.

d) 1-Biphenyl-4-yl-methyl-6-chloro-4-hydroxy-2-oxo-1,2-dihydro-pyrrolo[1,2-b]pyridazine-3-carboxylic acid methyl ester Prepared according to the cyclization condition used in Example 2 step g) from 1-[biphenyl-4-ylmethyl-(2-methoxycarbonyl-acetyl)-amino]-4-chloro-1H-pyrrole-2-carboxylic acid methyl ester. ESI (m/z): 409 (M+H)⁺.

e) 2-(S)-[(1-Biphenyl-4-ylmethyl-6-chloro-4-hydroxy-2-oxo-1,2-dihydro-pyrrolo[1,2-b]pyridazine-3-carbonyl)-amino]-propionic acid Prepared according to the reaction condition used in Example 19 step a) from 1-biphenyl-4-ylmethyl-6-chloro-4-hydroxy-2-oxo-1,2-dihydro-pyrrolo[1,2-b]pyridazine-3-carboxylic acid methyl ester, L-alanine and NaOMe. ESI (m/z): 466 (M+H)⁺.

Example 36

2-(R)-{[6-Chloro-1-(4-phenyl-benzyl)-4-hydroxy-2-oxo-1,2-dihydro-pyrrolo[1,2-b]pyridazine-3-carbonyl]-amino}-propionic acid a) 2-(R)-{[6-Chloro-1-(4-phenyl-benzyl)-4-hydroxy-2-oxo-1,2-dihydro-pyrrolo[1,2-b]pyridazine-3-carbonyl]-amino}-propionic acid Prepared according to the reaction condition used in Example 19 step a) from 6-chloro-4-hydroxy-2-oxo-1-(4-phenyl-benzyl)-1,2-dihydro-pyrrolo[1,2-b]pyridazine-3-carboxylic acid methyl ester, D-alanine and NaOMe. ESI (m/z): 466 (M+H)⁺.

Example 37

{[4-Hydroxy-2-oxo-6-phenyl-1-(4-trifluoromethyl-benzyl)-1,2-dihydro-pyrrolo[1,2-b]pyridazine-3-carbonyl]-amino}-acetic acid a) 1-Amino-4-bromo-1H-pyrrole-2-carboxylic acid methyl ester Prepared according to the N-amination condition used in Example 18 step a) from 4-bromo-1H-pyrrole-2-carboxylic acid methyl ester (prepared according to literature: *J. Chem. Soc. Perk I*, 1997, 1443-1448). ¹H NMR (CDCl₃, δ in ppm): 6.94 (d, 1H, J=2.2 Hz), 6.80 (d, 1H, J=2.2 Hz), 6.7-4.0 (very broad, 2H), 3.82 (s, 3H).

b) 4-Bromo-1-[(4-trifluoromethyl-benzylidene)-amino]-1H-pyrrole-2-carboxylic acid methyl ester Prepared according to the imine formation condition used in Example 18 step b) from 1-amino-4-bromo-1H-pyrrole-2-carboxylic acid methyl ester and 4-trifluoromethylbenzaldehyde. ¹H NMR (CDCl₃, δ in ppm): 8.44 (s, 1H), 7.96 (d, 2H, J=7.8 Hz), 7.70 (d, 2H, J=7.8 Hz), 7.27 (d, 1H, J=1.8 Hz), 6.99 (d, 1H, J=1.6 Hz), 3.85 (s, 3H).

c) 4-Bromo-1-(4-trifluoromethyl-benzylamino)-1H-pyrrole-2-carboxylic acid methyl ester Prepared according to the reduction condition used in Example 18 step c) from 4-bromo-1-[(4-trifluoromethyl-benzylidene)-amino]-1H-pyrrole-2-carboxylic acid methyl ester. ESI (m/z): 377 (M+H)⁺.

d) 4-Bromo-1-[(2-methoxycarbonyl-acetyl)-(4-trifluoromethyl-benzyl)-amino]-1H-pyrrole-2-carboxylic acid methyl ester Prepared according to the acylation condition used in Example 2 step f) from 4-bromo-1-(4-trifluoromethyl-benzylamino)-1H-pyrrole-2-carboxylic acid methyl ester (1.0 eq.) and chlorocarbonyl-acetic acid methyl ester (1.5 eq.). ESI (m/z): 477 (M+H)⁺.

e) 6-Bromo-4-hydroxy-2-oxo-1-(4-trifluoromethyl-benzyl)-1,2-dihydro-pyrrolo[1,2-b]pyridazine-3-carboxylic acid methyl ester Prepared according to the cyclization condition used in Example 2 step g) from 4-bromo-1-[(2-methoxycarbonyl-acetyl)-(4-trifluoromethyl-benzyl)-amino]-1H-pyrrole-2-carboxylic acid methyl ester. ¹H NMR (CDCl₃, δ in ppm): 14.1 (s, 1H), 7.61 (d, 2H, J=8.0 Hz), 7.40 (d, 2H, J=8.0 Hz), 6.95 (m, 2H), 5.50 (s, 2H), 4.02 (s, 3H).

f) 4-Hydroxy-2-oxo-6-phenyl-1-(4-trifluoromethyl-benzyl)-1,2-dihydro-pyrrolo[1,2-b]pyridazine-3-carboxylic acid methyl ester A mixture of 6-bromo-4-hydroxy-2-oxo-1-(4-trifluoromethyl-benzyl)-1,2-dihydro-pyrrolo[1,2-b]pyridazine-3-carboxylic acid methyl ester (446 mg), phenyl boronic acid (366 mg), PEPPSI-IPr (34 mg; Total Synthesis Ltd./Sigma-Aldrich), and sodium carbonate solution (1.0 mL, 2 M in water) in DMA (10 mL) was heated at 120° C. for 5 h; the mixture was then cooled, diluted with EtOAc, washed with water, diluted HCl solution and sat. NaCl solution respectively; subsequently, the organic phase was dried over sodium sulfate, filtered, concentrated, and the residue was column purified (eluent: DCM/MeOH) to give the desired product (59 mg). ESI (m/z): 443 (M+H)⁺.

g) {[4-Hydroxy-2-oxo-6-phenyl-1-(4-trifluoromethyl-benzyl)-1,2-dihydro-pyrrolo[1,2-b]pyridazine-3-carbonyl]-amino}-acetic acid Prepared according to the glycinolysis condition used in Example 1 step d) from 4-hydroxy-2-oxo-6-phenyl-1-(4-trifluoromethyl-benzyl)-1,2-dihydro-pyrrolo[1,2-b]pyridazine-3-carboxylic acid methyl ester (1.0 eq.) and sodium glycinate (5 eq.). ESI (m/z): 486 (M+H)⁺.

Example 38

[(6-Chloro-4-hydroxy-2-oxo-1-pyridin-3-ylmethyl-1,2-dihydro-pyrrolo[1,2-b]pyridazine-3-carbonyl)-amino]-acetic acid a) 4-Chloro-1-[(pyridin-3-ylmethylene)-amino]-1H-pyrrole-2-carboxylic acid methyl ester Prepared according to the imine formation condition used in Example 18 step b) from 1-amino-4-chloro-1H-pyrrole-2-carboxylic acid methyl ester and pyridine-3-carbaldehyde in refluxing methanol for 12 h. ¹H NMR (CDCl₃, δ in ppm): 8.43 (s, 1H), 8.29-8.13 (m, 2H), 7.51-7.43 (m, 2H), 7.23 (d, 1H, J=1.8 Hz), 6.91 (d, 1H, J=1.8 Hz), 3.84 (s, 3H).

b) 4-Chloro-1-[(pyridin-3-ylmethyl)-amino]-1H-pyrrole-2-carboxylic acid methyl ester Prepared according to the reduction condition used in Example 18 step c) from 4-chloro-1-[(pyridin-3-ylmethylene)-amino]-1H-pyrrole-2-carboxylic acid methyl ester. ¹H NMR (CDCl₃, δ in ppm): 8.56-8.49 (m, 2H), 7.61-7.56 (m, 1H), 7.28-7.22 (m, 1H), 6.74 (d, 1H, J=2.2 Hz), 6.70 (d, 1H, J=2.2 Hz), 6.59 (t, 1H, J=5.5 Hz), 4.11 (d, 2H, J=5.4 Hz), 3.83 (s, 3H).

c) 4-Chloro-1-[(2-methoxycarbonyl-acetyl)-pyridin-3-ylmethyl-amino]-1H-pyrrole-2-carboxylic acid methyl ester Prepared according to the acylation condition used in Example 2 step f) from 4-chloro-1-[(pyridin-3-ylmethyl)-amino]-1H-pyrrole-2-carboxylic acid methyl ester and chlorocarbonyl-acetic acid methyl ester (1.5 eq.). ¹H NMR (CDCl₃, δ in ppm): 8.55 (dd, 1H, J=1.8 Hz, 4.8 Hz), 8.34 (1H, J=2.2 Hz), 7.57 (m, 1H), 6.84 (d, 1H, J=2.2 Hz), 6.50 (d, 1.8 Hz), 5.29 (d, 1H, J=14.6 Hz), 4.45 (d, J=14.6 Hz), 3.76 (s, 3H), 3.69 (s, 3H), 3.19 (m, 2H).

d) 6-Chloro-4-hydroxy-2-oxo-1-pyridin-3-ylmethyl-1,2-dihydro-pyrrolo[1,2-b]pyridazine-3-carboxylic acid methyl ester Prepared according to the cyclization condition used in Example 2 step g) from 4-chloro-1-[(2-methoxycarbonyl-acetyl)-pyridin-3-ylmethyl-amino]-1H-pyrrole-2-carboxylic acid methyl ester. ESI (m/z): 334 (M+H)⁺.

e) [(6-Chloro-4-hydroxy-2-oxo-1-pyridin-3-ylmethyl-1,2-dihydro-pyrrolo[1,2-b]pyridazine-3-carbonyl)-amino]-acetic acid Prepared according to the glycinolysis condition used in Example 1 step d) from 6-chloro-4-hydroxy-2-oxo-1-pyridin-3-ylmethyl-1,2-dihydro-pyrrolo[1,2-b]pyridazine-3-carboxylic acid methyl ester (1.0 eq.) and sodium glycinate (5 eq.). ESI (m/z): 377 (M+H)⁺.

Example 39

2-(S)-[(6-Chloro-4-hydroxy-2-oxo-1-pyridin-3-ylmethyl-1,2-dihydro-pyrrolo[1,2-b]pyridazine-3-carbonyl)-amino]-propionic acid Prepared according to the reaction condition used in Example 19 step a) from 6-chloro-4-hydroxy-2-oxo-1-pyridin-3-ylmethyl-1,2-dihydro-pyrrolo[1,2-b]pyridazine-3-carboxylic acid methyl ester, L-alanine and NaOMe. ESI (m/z): 391 (M+H)⁺.

Example 40

[(6-Chloro-4-hydroxy-2-oxo-1-pyridin-2-ylmethyl-1,2-dihydro-pyrrolo[1,2-b]pyridazine-3-carbonyl)-amino]-acetic acid a) 4-Chloro-1-[(pyridin-2-ylmethylene)-amino]-1H-pyrrole-2-carboxylic acid methyl ester Prepared according to the imine formation condition used in Example 18 step b) from 1-amino-4-chloro-1H-pyrrole-2- carboxylic acid methyl ester and pyridine-2-carbaldehyde in refluxing methanol for 12 h. $^1$H NMR (CDCl$_3$, δ in ppm): 8.67 (dt, 1H, J=1.3 Hz, 5.0 Hz), 8.48 (s, 1H), 8.21 (dt, 1H, J=1.1 Hz, 8.4 Hz), 7.79 (td, 1H, J=1.8 Hz, 7.8 Hz), 7.36 (m, 1H, J=1.0 Hz, 5.0 Hz, 7.6 Hz), 7.30 (d, 1H, J=2.2 Hz), 6.91 (d, 1H, J=1.8 Hz), 3.86 (s, 3H).

b) 4-Chloro-1-[(pyridin-2-ylmethyl)-amino]-1H-pyrrole-2-carboxylic acid methyl ester Prepared according to the reduction condition used in Example 18 step c) from 4-chloro-1-[(pyridin-2-ylmethylene)-amino]-1H-pyrrole-2-carboxylic acid methyl ester. $^1$H NMR (CDCl$_3$, δ in ppm): 8.60 (m, 1H), 7.67 (m, 1H), 7.28-7.18 (m, 2H), 6.92-6.84 (m, 1H), 6.79 (d, 1H, J=2.2 Hz), 6.74 (d, 1H, J=2.2 Hz), 4.27 (d, 2H, J=4.8 Hz), 3.83 (s, 3H).

c) 4-Chloro-1-[(2-methoxycarbonyl-acetyl)-pyridin-2-ylmethyl-amino]-1H-pyrrole-2-carboxylic acid methyl ester Prepared according to the acylation condition used in Example 2 step f) from 4-chloro-1-[(pyridin-2-ylmethyl)-amino]-1H-pyrrole-2-carboxylic acid methyl ester and chlorocarbonyl-acetic acid methyl ester (1.5 eq.). $^1$H NMR (CDCl$_3$, δ in ppm): 8.5 (m, 1H), 7.68 (m, 1H), 7.39 (m, 1H), 721 (m, 1H), 6.85 (d, 1H, J=1.6 Hz), 6.80 (d, 1H, J=1.6 Hz), 5.48 (d, 1H, J=15.4 Hz), 4.46 (d, 1H, J=15.4 Hz), 3.79 (s, 3H), 3.69 (s, 3H), 3.19 (s, 2H).

d) 6-Chloro-4-hydroxy-2-oxo-1-pyridin-2-ylmethyl-1,2-dihydro-pyrrolo[1,2-b]pyridazine-3-carboxylic acid methyl ester Prepared according to the cyclization condition used in Example 2 step g) from 4-chloro-1-[(2-methoxycarbonyl-acetyl)-pyridin-2-ylmethyl-amino]-1H-pyrrole-2-carboxylic acid methyl ester. $^1$H NMR (CDCl$_3$, δ in ppm): 14.0 (s, 1H), 8.57 (m, 1H), 7.67 (dt, 1H, J=1.8 Hz, 7.4 Hz), 7.53 (d, 1H, J=1.6 Hz), 7.39 (d, 1H, J=8.0 Hz), 7.24 (m, 1H), 6.84 (d, 1H, J=1.8 Hz), 5.53 (s, 2H), 4.02 (s, 3H).

e) [(6-Chloro-4-hydroxy-2-oxo-1-pyridin-2-ylmethyl-1,2-dihydro-pyrrolo[1,2-b]pyridazine-3-carbonyl)-amino]-acetic acid Prepared according to the glycinolysis condition used in Example 1 step d) from 6-chloro-4-hydroxy-2-oxo-1-pyridin-2-ylmethyl-1,2-dihydro-pyrrolo[1,2-b]pyridazine-3-carboxylic acid methyl ester (1.0 eq.) and sodium glycinate (5 eq.). ESI (m/z): 377 (M+H)$^+$.

Example 41

2-(S)-[(6-Chloro-4-hydroxy-2-oxo-1-pyridin-2-ylmethyl-1,2-dihydro-pyrrolo[1,2-b]pyridazine-3-carbonyl)-amino]-propionic acid Prepared according to the reaction condition used in Example 19 step a) from 6-chloro-4-hydroxy-2-oxo-1-pyridin-2-ylmethyl-1,2-dihydro-pyrrolo[1,2-b]pyridazine-3-carboxylic acid methyl ester, L-alanine and NaOMe. ESI (m/z): 391 (M+H)$^+$.

Example 42

{[6,7-Dichloro-1-(4-fluoro-benzyl)-4-hydroxy-2-oxo-1,2-dihydro-pyrrolo[1,2-b]pyridazine-3-carbonyl]-amino}-acetic acid a) 4,5-Dichloro-1-(1,3-dioxo-1,3-dihydro-isoindol-2-yl)-1i-pyrrole-2-carboxylic acid methyl ester A mixture of 1-(1,3-dioxo-1,3-dihydro-isoindol-2-yl)-1H-pyrrole-2-carboxylic acid methyl ester (4.43 g, prepared according to literature: *J. Org. Chem.*, 1997, 62, 2894-2906) and NCS (4.58 g) in DMF (100 mL) was heated at 50 to 60° C. (oil bath temperature) for 6 h. Then reaction was cooled and DMF was rotovaped, the residue was dissolved in EtOAc, and then washed with diluted sodium bicarbonate solution, water and sat. NaCl solution, respectively, then dried over anhydrous sodium sulfate, filtered, concentrated to give crude product (5.44 g), which is sufficiently pure for the next step. $^1$H NMR (CDCl$_3$, δ in ppm): 8.1-7.8 (m, 4H), 7.04 (s, 1H), 3.70 (s, 3H).

b) 1-Amino-4,5-dichloro-1H-pyrrole-2-carboxylic acid methyl ester

A mixture of 4,5-dichloro-1-(1,3-dioxo-1,3-dihydro-isoindol-2-yl)-1H-pyrrole-2-carboxylic acid methyl ester (5.44 g) and hydrazine monohydrate (1.57 mL) in ethanol was stirred at rt overnight, by which time TLC showed complete conversion; then the solids were filtered off, the filtrate was concentrated and worked up with EtOAc and water; EtOAc phase was washed with sat. NaCl solution and dried over anhydrous sodium sulfate, filtered, concentrated, the crude was column purified (EtOAc/Hexanes) to give desired product (2.21 g). ESI (m/z): 209 (M+H)$^+$.

c) 4,5-Dichloro-1-[(4-fluoro-benzylidene)-amino]-1H-pyrrole-2-carboxylic acid methyl ester Prepared according to the imine formation condition used in Example 18 step b) from 1-amino-4,5-dichloro-1H-pyrrole-2-carboxylic acid methyl and 4-fluoro benzaldehyde in refluxing methanol for 12 h. $^1$H NMR (CDCl$_3$, δ in ppm): 8.44 (s, 1H), 7.89 (m, 2H), 7.17 (m, 2H), 6.97 (s, 1H), 3.77 (s, 3H).

d) 4,5-Dichloro-1-(4-fluoro-benzylamino)-1H-pyrrole-2-carboxylic acid methyl ester Prepared according to the reduction condition used in Example 18 step c) from 4,5-dichloro-1-[(4-fluoro-benzylidene)-amino]-1H-pyrrole-2-carboxylic acid methyl ester. $^1$H NMR (CDCl$_3$, δ in ppm): 7.31 (dd, 2H, J=5.2 Hz, 8.8 Hz), 7.01 (t, J=8.6 Hz), 6.80 (s, 1H), 6.46 (t, 1H), 4.05 (d, 2H, J=6.6 Hz), 3.83 (s, 3H).

e) 4,5-Dichloro-1-[(4-fluoro-benzyl)-(2-methoxycarbonyl-acetyl)-amino]-1H-pyrrole-2-carboxylic acid methyl ester Prepared according to the acylation condition used in Example 2 step f) from 4,5-dichloro-1-(4-fluoro-benzylamino)-1H-pyrrole-2-carboxylic acid methyl ester and chlorocarbonyl-acetic acid methyl ester (1.5 eq.). $^1$H NMR (CDCl$_3$, δ in ppm): 7.1-6.8 (m, 5H), 4.88 (d, 1H, J=14.6 Hz), 4.75 (d, 1H, J=14.0 Hz), 3.72 (s, 3H), 3.67 (s, 3H), 3.17 (dd, 2H).

f) 6,7-Dichloro-1-(4-fluoro-benzyl)-4-hydroxy-2-oxo-1,2-dihydro-pyrrolo[1,2-b]pyridazine-3-carboxylic acid methyl ester Prepared according to the cyclization condition used in Example 2 step g) from 4,5-dichloro-1-[(4-fluoro-benzyl)-(2-methoxycarbonyl-acetyl)-amino]-1H-pyrrole-2-carboxylic acid methyl ester. ESI (m/z): 385 (M+H)$^+$.

g) {[6,7-Dichloro-1-(4-fluoro-benzyl)-4-hydroxy-2-oxo-1,2-dihydro-pyrrolo[1,2-b]pyridazine-3-carbonyl]-amino}-acetic acid Prepared according to the glycinolysis condition used in Example 1 step d) from 6,7-Dichloro-1-(4-fluoro-benzyl)-4-hydroxy-2-oxo-1,2-dihydro-pyrrolo[1,2-b]pyridazine-3-carboxylic acid methyl ester (1.0 eq.) and sodium glycinate (5 eq.). ESI (m/z): 428 (M+H)$^+$.

Example 43

{[4-(4-Fluoro-benzyl)-1-hydroxy-3-oxo-6-trifluoromethyl-3,4-dihydro-4,4a-diaza-fluorene-2-carbonyl]-amino}-acetic acid

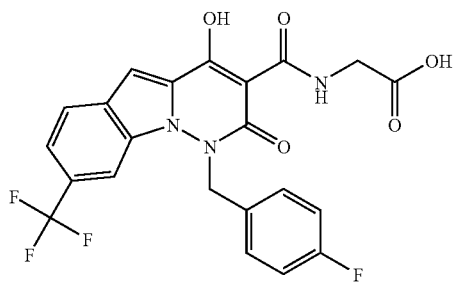

a) 1-Amino-6-trifluoromethyl-1H-indole-2-carboxylic acid ethyl ester

Prepared according to the condition used in Example 18 step a) from 6-trifluoromethyl-1H-indole-2-carboxylic acid ethyl ester (prepared according to literature: Bornstein J. et al; *Journal of the American Chemical Society* 1957, 79, 1745-1747). ESI (m/z): 273.19 (M+H)$^+$.

b) 1-(4-Fluoro-benzylamino)-6-trifluoromethyl-1H-indole-2-carboxylic acid ethyl ester A mixture of 1-amino-6-trifluoromethyl-1H-indole-2-carboxylic acid ethyl ester (2.0 g, 7.36 mmol) and 4-fluorobenzaldehyde (14.72 mmol) in ethanol (20 mL) was refluxed for 18 h. Reaction mixture, after cooled down to 0° C., was diluted with hexanes (20 ml). Solid was collected, rinsed with hexanes and dried in vacuo to give the imine intermediate 1.76 g (4.66 mmol). The intermediate was dissolved in (1/1) ethanol/THF (25 ml) and then added sodium borohydride (194 mg, 5.12 mmol). The resultant mixture was refluxed for 4 h and, after cooled to rt, was quenched with 1 N HCl solution (10 mL). The mixture was then adjusted to basic (pH=8-9) by adding saturated NaHCO$_3$ solution and more water was added to clear two phases. Organic layer was washed with brine, dried over MgSO$_4$, filtered and concentrated. Crude product was purified by silica gel chromatography (50%-100% DCM/hexanes) to provide the title compound as a white solid (0.9 g). ESI (m/z): 381.18 (M+H)$^+$.

c) 1-[(2-Ethoxycarbonyl-acetyl)-(4-fluoro-benzyl)-amino]-6-trifluoromethyl-1H-indole-2-carboxylic acid ethyl ester A mixture of 1-(4-fluoro-benzylamino)-6-trifluoromethyl-1H-indole-2-carboxylic acid ethyl ester (240 mg, 0.63 mmol) and chlorocarbonyl-acetic acid ethyl ester (105 mg, 0.69 mmol) in dioxane (3 mL) was heated in an 100° C. oil bath for 30 min and concentrated. Crude product was purified by silica gel chromatography (5%-50% EtOAc/DCM) to provide the title compound 162 mg. ESI (m/z): 495.24 (M+H)$^+$.

d) 4-(4-Fluoro-benzyl)-1-hydroxy-3-oxo-6-trifluoromethyl-3,4-dihydro-4,4a-diaza-fluorene-2-carboxylic acid methyl ester A mixture of 1-[(2-ethoxycarbonyl-acetyl)-(4-fluoro-benzyl)-amino]-6-trifluoromethyl-1H-indole-2-carboxylic acid ethyl ester (160 mg, 0.32 mmol) in 0.5 N NaOMe/MeOH solution (2.5 mL, 1.25 mmol) was refluxed overnight. After cooled, the mixture was concentrated, and the residue was dissolved in water (80 mL), acidified to pH=3-4 using 1 N HCl solution, extracted with EtOAc (2 times). Combined organic layers were washed with brine, dried over MgSO$_4$, filtered and concentrated. Crude product was purified by silica gel chromatography (50%-100% EtOAc/DCM then 2%-10% MeOH/DCM) to provide the title compound 31 mg. ESI (m/z): 435.14 (M+H)$^+$.

e) {[4-(4-Fluoro-benzyl)-1-hydroxy-3-oxo-6-trifluoromethyl-3,4-dihydro-4,4a-diaza-fluorene-2-carbonyl]-amino}-acetic acid A mixture of 4-(4-fluoro-benzyl)-1-hydroxy-3-oxo-6-trifluoromethyl-3,4-dihydro-4,4a-diaza-fluorene-2-carboxylic acid methyl ester (100 mg, 0.23 mmol) and sodium glycinate (224 mg, 2.3 mmol) in 2-methoxyethanol (3.3 mL) was microwaved at 150° C. for 1 h and concentrated. Residue was dissolved in water (80 mL) and acidified to pH=3-4 using 1 N HCl solution. Precipitate was collected and rinsed with water. Solid was then dissolved in EtOAc, dried over MgSO$_4$, filtered and concentrated. Crude product was triturated in MeOH (3 mL) and solid was collected and dried in vacuo to provide the title compound 62 mg. ESI (m/z): 476.01 (M–H)$^-$

Example 44

2-(S)-{[4-(4-Fluoro-benzyl)-1-hydroxy-3-oxo-6-trifluoromethyl-3,4-dihydro-4,4a-diaza-fluorene-2-carbonyl]-amino}-propionic acid

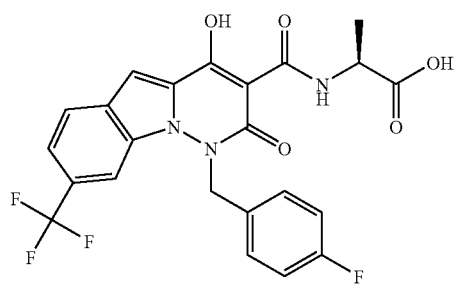

a) 2-(S)-{[4-(4-Fluoro-benzyl)-1-hydroxy-3-oxo-6-trifluoromethyl-3,4-dihydro-4,4a-diaza-fluorene-2-carbonyl]-amino}-propionic acid A mixture of 4-(4-fluoro-benzyl)-1-hydroxy-3-oxo-6-trifluoromethyl-3,4-dihydro-4,4a-diaza-fluorene-2-carboxylic acid methyl ester (compound 43 d) (100 mg, 0.23 mmol), L-alanine (205 mg, 2.3 mmol) and sodium methoxide (99 mg, 1.84 mmol) in 2-methoxyethanol (3.5 mL) was microwaved at 150° C. for 2 h and concentrated. Residue was dissolved in water (80 mL), acidified to pH=3-4 using 1 N HCl solution and extracted with EtOAc. Organic layer was washed with brine, dried over $MgSO_4$, filtered and concentrated. Crude product was purified by silica gel chromatography (15%-70% EtOAc (with 0.075% HOAc)/hexanes (with 0.1% HOAc)) to provide the title compound 34 mg. ESI (m/z): 490.03 (M−H)⁻.

We claim:
1. A compound of Formula I:

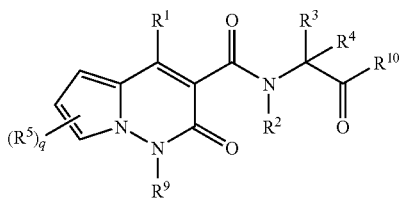

I wherein:
q is 0, 1, 2 or 3;
$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino;
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, alkyl, and substituted alkyl;
each $R^5$ independently is selected from the group consisting of hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl; or wherein any two adjacent $R^5$ groups, together with the carbon atoms attached thereto, join to form an aryl, heteroaryl or cycloalkenyl group optionally substituted with 1 to 4 substituents independently selected from halogen, alkyl, substituted alkyl, alkoxy, substituted alkoxy, aryl, and substituted aryl;
$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;
$R^{10}$ is —$NR^{11}R^{12}$ or —$OR^{13}$;
$R^{11}$ and $R^{12}$ independently are selected from the group consisting of hydrogen, alkyl, cycloalkyl-alkyl, $C_3$-$C_8$ heterocyclic, aryl, and —$C(O)C_1$-$C_4$ alkyl;
or $R^{11}$ and $R^{12}$ taken together with the nitrogen to which they are attached form a 5- or 6-membered heterocyclic or substituted heterocyclic; and
$R^{13}$ is selected from the group consisting of hydrogen and alkyl optionally substituted with one or more substituents independently selected from the group consisting of cycloalkyl, heterocyclic, aryl, and heteroaryl;
or a pharmaceutically acceptable salt, single stereoisomer, mixture of stereoisomers, or tautomer thereof.

2. A compound of formula II:

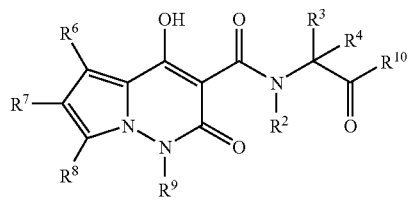

II wherein
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, alkyl, and substituted alkyl;
$R^6$, $R^7$ and $R^8$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;
or wherein $R^6$ and $R^7$, or $R^7$ and $R^8$, together with the carbons to which they are attached, form a 5- or 6-membered heteroaryl group or a 6-membered aryl group, optionally substituted independently by one or two substituents selected from the group consisting of halogen, alkyl, substituted alkyl, alkoxy, substituted alkoxy, aryl, and substituted aryl;
$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is —$NR^{11}R^{12}$ or —$OR^{13}$;

$R^{11}$ and $R^{12}$ are independently selected from the group consisting of hydrogen, alkyl, cycloalkyl-alkyl, $C_3$-$C_8$ heterocyclic, aryl, and —C(O)($C_1$-$C_4$ alkyl);

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl optionally substituted with one or more substituents independently selected from the group consisting of cycloalkyl, heterocyclic, aryl, and heteroaryl;

or a pharmaceutically acceptable salt, single stereoisomer, mixture of stereoisomers, or tautomer thereof.

3. A compound of formula III:

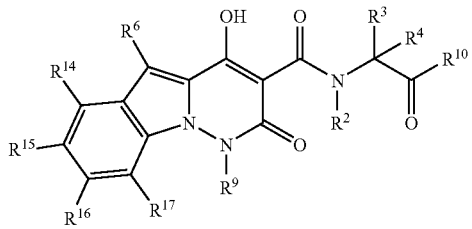

wherein $R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, alkyl, and substituted alkyl;

$R^6$ is selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyl, substituted cycloalkyl, cycloalkyloxy, substituted cycloalkyloxy, heterocyclyloxy, substituted heterocyclyloxy, carboxyl, carboxyl ester, carboxylamide, oxycarbonylamino, aminocarbonyloxy, aminocarbonylamino, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;

$R^{14}$, $R^{15}$, $R^{16}$, and $R^{17}$ independently are selected from the group consisting of hydrogen, halogen, alkyl, substituted alkyl, alkoxy, substituted alkoxy, aryl, and substituted aryl;

$R^9$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

$R^{10}$ is —$NR^{11}R^{12}$ or —$OR^{13}$;

$R^{11}$ and $R^{12}$ independently are selected from the group consisting of hydrogen, alkyl, cycloalkyl-alkyl, $C_3$-$C_8$ heterocyclic, aryl, and —C(O)($C_1$-$C_4$ alkyl);

or $R^{11}$ and $R^{12}$ taken together with the nitrogen to which they are attached form a 5- or 6-membered heterocyclic or substituted heterocyclic; and $R^{13}$ is selected from the group consisting of hydrogen and alkyl optionally substituted with one or more substituents independently selected from the group consisting of cycloalkyl, heterocyclic, aryl, and heteroaryl;

or a pharmaceutically acceptable salt, single stereoisomer, mixture of stereoisomers, or tautomer thereof.

4. The compound of claim 1, wherein q is 0 or 1.

5. The compound of claim 1, wherein $R^1$ is hydroxy.

6. The compound of claim 1, wherein $R^1$ is hydroxy and $R^2$ is hydrogen.

7. The compound of claim 1, wherein $R^1$ is hydroxy; and $R^2$ and $R^3$ are hydrogen.

8. The compound of claim 1, wherein $R^1$ is hydroxy; and $R^2$, $R^3$, and $R^4$ are hydrogen.

9. The compound of claim 1, wherein each $R^5$ is independently selected from the group consisting of halo and aryl.

10. The compound of claim 1, wherein each $R^5$ is selected from the group consisting of hydrogen, chloro, and phenyl.

11. The compound of claim 1, wherein $R^9$ is hydrogen.

12. The compound of claim 1, wherein $R^9$ is selected from the group consisting of hydrogen, alkyl, —$CH_2$-aryl, —$CH_2$-substituted aryl, —$CH_2$-cycloalkyl, —$CH_2$-substituted cycloalkyl, —$CH_2$-heterocyclic, —$CH_2$-substituted heterocyclic, —$CH_2$-heteroaryl and —$CH_2$-substituted heteroaryl.

13. The compound of claim 1, wherein $R^9$ is —$CH_2$-aryl or —$CH_2$-substituted aryl.

14. The compound of claim 12, wherein substituted aryl is substituted with fluoro, chloro, trifluoromethyl, or methoxy.

15. The compound of claim 1, wherein $R^{10}$ is —$OR^{13}$; and $R^{13}$ is selected from the group consisting of hydrogen and alkyl optionally substituted with one or more substituents independently selected from the group consisting of cycloalkyl, heterocyclic, aryl, and heteroaryl.

16. The compound of claim 1, wherein $R^1$ is hydroxy;

$R^2$ and $R^3$ are hydrogen; and each $R^5$ is independently selected from the group consisting of halo, alkyl, substituted alkyl, aryl, substituted aryl, alkoxy, substituted alkoxy, aryloxy, substituted aryloxy, arylthio, substituted arylthio, heteroaryl, and substituted heteroaryl.

17. The compound of claim 1, wherein q is 1;

$R^1$ is hydroxy;

$R^2$ and $R^3$ are hydrogen;

each $R^5$ is independently selected from the group consisting of halo, alkyl, substituted alkyl, aryl, substituted aryl, alkoxy, substituted alkoxy, aryloxy, substituted aryloxy, arylthio, substituted arylthio, heteroaryl, and substituted heteroaryl; and $R^{10}$ is —$OR^{13}$; wherein $R^{13}$ is hydrogen or alkyl.

18. The compound of claim 1, wherein q is 0;

$R^1$ is hydroxy;

$R^2$ and $R^3$ are hydrogen;

$R^4$ is selected from the group consisting of hydrogen, methyl, and ethyl;

$R^9$ is selected from the group consisting of hydrogen, alkyl, —$CH_2$-aryl, —$CH_2$-substituted aryl, and —$CH_2$-heteroaryl; and $R^{10}$ is —$OR^{13}$; wherein $R^{13}$ is hydrogen or alkyl.

19. A compound selected from the group consisting of [(1-Benzyl-4-hydroxy-2-oxo-1,2-dihydro-pyrrolo[1,2-b]pyridazine-3-carbonyl)-amino]-acetic acid; [(1-Benzyl-5,6,7-trichloro-4-hydroxy-2-oxo-1,2-dihydro-pyrrolo[1,2-b]pyridazine-3-carbonyl)-amino]-acetic acid; {[1-(4-Fluoro-benzyl)-4-hydroxy-2-oxo-1,2-dihydro-pyrrolo[1,2-b]pyridazine-3-carbonyl]-amino}-acetic acid; [(4-Hydroxy-2-oxo-1,2-dihydro-pyrrolo[1,2-b]pyridazine-3-carbonyl)-amino]-acetic acid; {[1-(2-Fluoro-benzyl)-4-hydroxy-2-oxo-1,2-dihydro-pyrrolo[1,2-b]pyridazine-3-carbonyl]-amino}-acetic acid; {[1-(2,4-Difluoro-benzyl)-4-hydroxy-2-oxo-1,2-dihydro-pyrrolo[1,2-b]pyridazine-3-carbonyl]-amino}-acetic acid; {[1-(2-Chloro-benzyl)-4-hydroxy-2-oxo-1,2-dihydro-pyrrolo[1,2-b]pyridazine-3-carbonyl]-amino}-acetic acid; {[1-(3-Chloro-benzyl)-4-hydroxy-2-oxo-1,2-dihydro-pyrrolo[1,2-b]pyridazine-3-carbonyl]-amino}-acetic acid; [(4-Hydroxy-1-naphthalen-2-ylmethyl-2-oxo-1,2-dihydro-pyrrolo[1,2-b]pyridazine-3-carbonyl)-amino]-acetic acid; {[4-Hydroxy-2-oxo-1-(4-trifluoromethyl-benzyl)-1,2-dihydro-pyrrolo[1,2-b]pyridazine-3-carbonyl]-amino}-acetic acid; {[1-(4-Chloro-benzyl)-4-hydroxy-2-oxo-1,2-dihydro-pyrrolo[1,2-b]pyridazine-3-carbonyl]-amino}-acetic acid; {[4-Hydroxy-1-(4-methoxy-benzyl)-2-oxo-1,2-dihydro-pyrrolo[1,2-b]pyridazine-3-carbonyl]-amino}-acetic acid; {[4-Hydroxy-oxo-1-(3-trifluoromethyl-benzyl)-1,2-dihydro-pyrrolo[1,2-b]pyridazine-3-carbonyl]-amino}-acetic acid; {[1-(3-Fluoro-benzyl)-4-hydroxy-2-oxo-1,2-dihydro-pyrrolo[1,2-b]pyridazine-3-carbonyl]-amino}-acetic acid; {[1-(2,6-Difluoro-benzyl)-4-hydroxy-2-oxo-1,2-dihydro-pyrrolo[1,2-b]pyridazine-3-carbonyl]-amino}-acetic acid; {[4-Hydroxy-2-oxo-1-(2-trifluoromethyl-benzyl)-1,2-dihydro-pyrrolo[1,2-b]pyridazine-3-carbonyl]-amino}-acetic acid; [(1-Butyl-4-hydroxy-2-oxo-,2-dihydro-pyrrolo[1,2-b]pyridazine-3-carbonyl)-amino]-acetic acid; {[4-(4-Fluoro-benzyl)-1-hydroxy-3-oxo-3,4-dihydro-4,4-a-diaza-fluorene-2-carbonyl]-amino}-acetic acid; 2-(S)-{[4-(4-Fluoro-benzyl)-1-hydroxy-3-oxo-3,4-dihydro-4,4-a-diaza-fluorene-2-carbonyl]-amino}-propionic acid; [(1-Hexyl-4-hydroxy-2-oxo-1,2-dihydro-pyrrolo[1,2-b]pyridazine-3-carbonyl)-amino]-acetic acid; {[7-Fluoro-4-(4-fluoro-benzyl)-1-hydroxy-3-oxo-3,4-dihydro-4,4-a-diaza-fluorene-2-carbonyl]-amino}-acetic acid; {[6-Chloro-4-hydroxy-2-oxo-1-(4-trifluoromethyl-benzyl)-1,2-dihydro-pyrrolo[1,2-b]pyridazine-3-carbonyl]-amino}-acetic acid; 2-(S)-{[6-Chloro-4-hydroxy-2-oxo-1-(4-trifluoromethyl-benzyl)-1,2-dihydro-pyrrolo[1,2-b]pyridazine-3-carbonyl]-amino}-propionic acid; 2-(S)-{[4-Hydroxy-2-oxo-1-(4-trifluoromethyl-benzyl)-1,2-dihydro-pyrrolo[1,2-b]pyridazine-3-carbonyl]-amino}-propionic acid; 2-(S)-{[4-Hydroxy-2-oxo-1-(4-trifluoromethyl-benzyl)-1,2-dihydro-pyrrolo[1,2-b]pyridazine-3-carbonyl]-amino}-butyric acid; {[6-Chloro-4-hydroxy-2-oxo-1-(4-fluoro-benzyl)-1,2-dihydro-pyrrolo[1,2-b]pyridazine-3-carbonyl]-amino}-acetic acid; 2-(S)-{[6-Chloro-1-(4-fluoro-benzyl)-4-hydroxy-2-oxo-1,2-dihydro-pyrrolo[1,2-b]pyridazine-3-carbonyl]-amino}-propionic acid; {[6-Chloro-1-(4-chloro-benzyl)-4-hydroxy-2-oxo-1,2-dihydro-pyrrolo[1,2-b]pyridazine-3-carbonyl]-amino}-acetic acid; 2-(S)-{[6-Chloro-1-(4-chloro-benzyl)-4-hydroxy-2-oxo-1,2-dihydro-pyrrolo[1,2-b]pyridazine-3-carbonyl]-amino}-propionic acid; 2-(S)-{[6-Chloro-1-(4-chloro-benzyl)-4-hydroxy-2-oxo-1,2-dihydro-pyrrolo[1,2-b]pyridazine-3-carbonyl]-amino}-butyric acid; {[6-Chloro-1-(4-methoxy-benzyl)-4-hydroxy-2-oxo-1,2-dihydro-pyrrolo[1,2-b]pyridazine-3-carbonyl]-amino}-acetic acid; 2-(S)-{[6-Chloro-1-(4-methoxy-benzyl)-4-hydroxy-2-oxo-1,2-dihydro-pyrrolo[1,2-b]pyridazine-3-carbonyl]-amino}-propionic acid; 2-(S)-{[6-Chloro-1-(4-methoxy-benzyl)-4-hydroxy-2-oxo-1,2-dihydro-pyrrolo[1,2-b]pyridazine-3-carbonyl]-amino}-butyric acid; 2-(S)-{[6-Chloro-1-(4-fluoro-benzyl)-4-hydroxy-2-oxo-1,2-dihydro-pyrrolo[1,2-b]pyridazine-3-carbonyl]-amino}-butyric acid; 2-(S)-[(1-Biphenyl-4-ylmethyl-6-chloro-4-hydroxy-2-oxo-1,2-dihydro-pyrrolo[1,2-b]pyridazine-3-carbonyl)-amino]-propionic acid; 2-(R)-{[6-Chloro-1-(4-phenyl-benzyl)-4-hydroxy-2-oxo-1,2-dihydro-pyrrolo[1,2-b]pyridazine-3-carbonyl]-amino}-propionic acid; {[4-Hydroxy-2-oxo-6-phenyl-1-(4-trifluoromethyl-benzyl)-1,2-dihydro-pyrrolo[1,2-b]pyridazine-3-carbonyl]-amino}-acetic acid; [(6-Chloro-4-hydroxy-2-oxo-1-pyridin-3-ylmethyl-1,2-dihydro-pyrrolo[1,2-b]pyridazine-3-carbonyl)-amino]-acetic acid; 2-(S)-[(6-Chloro-4-hydroxy-2-oxo-1-pyridin-3-ylmethyl-1,2-dihydro-pyrrolo[1,2-b]pyridazine-3-carbonyl)-amino]-propionic acid; [(6-Chloro-4-hydroxy-2-oxo-1-pyridin-2-ylmethyl-1,2-dihydro-pyrrolo[1,2-b]pyridazine-3-carbonyl)-amino]-acetic acid; 2-(S)-[(6-Chloro-4-hydroxy-2-oxo-1-pyridin-2-ylmethyl-1,2-dihydro-pyrrolo[1,2-b]pyridazine-3-carbonyl)-amino]-propionic acid; {[6,7-Dichloro-1-(4-fluoro-benzyl)-4-hydroxy-2-oxo-1,2-dihydro-pyrrolo[1,2-b]pyridazine-3-carbonyl]-amino}-acetic acid; {[4-(4-Fluoro-benzyl)-1-hydroxy-3-oxo-6-trifluoromethyl-3,4-dihydro-4,4-a-diaza-fluorene-2-carbonyl]-amino}-acetic acid; and 2-(S)-{[4-(4-Fluoro-benzyl)-1-hydroxy-3-oxo-6-trifluoromethyl-3,4-dihydro-4,4-a-diaza-fluorene-2-carbonyl]-amino}-propionic acid; or a pharmaceutically acceptable salt, single stereoisomer, mixture of stereoisomers, or tautomer thereof.

20. A pharmaceutical composition comprising one or more compounds of claim 1 and a pharmaceutically acceptable excipient.

21. The composition of claim 20 further comprising at least one therapeutic agent selected from the group consisting of vitamin $B_{12}$, folic acid, ferrous sulfate, recombinant human erythropoietin, and an erythropoiesis stimulating agent (ESA).

22. A method of treating a condition mediated at least in part by hypoxia inducible factor (HIF), the method comprising administering to a patient a therapeutically effective amount of a composition of claim 20.

23. The method of claim 22, wherein the condition mediated at least in part by HIF is tissue damage associated with ischemia or hypoxia.

24. The method of claim 23, wherein the ischemia is associated with an event selected from the group consisting of myocardial infarction, pulmonary embolism, intestinal infarction, ischemic stroke, and renal ischemic-reperfusion injury.

25. The method of claim 23, wherein the ischemia is associated with an event selected from the group consisting of cardiac cirrhosis, macular degeneration, transient ischemic attack, peripheral artery disease, chronic kidney failure, and congestive heart failure.

26. A method of treating a condition mediated at least in part by erythropoietin (EPO), the method comprising administering to a patient a therapeutically effective amount of a composition of claim 20.

27. A method of treating anemia, the method comprising administering to a patient a therapeutically effective amount of a composition of claim 20.

28. A method of inhibiting the activity of a HIF hydroxylase enzyme, the method comprising bringing into contact the HIF hydroxylase enzyme and an inhibitory-effective amount of a compound of claim 1.

29. The method of claim 28, wherein the HIF hydroxylase enzyme is an asparaginyl hydroxylase.

30. The method of claim 29, wherein the asparaginyl hydroxylase is a factor inhibiting HIF (FIH).

31. The method of claim 28, wherein the HIF hydroxylase enzyme is a prolyl hydroxylase.

32. The method of claim 31, wherein the prolyl hydroxylase is selected from the group consisting of human EGLN1, EGLN2, and EGLN3.

\* \* \* \* \*